United States Patent [19]

Mazer et al.

[11] Patent Number: 5,160,742
[45] Date of Patent: Nov. 3, 1992

[54] SYSTEM FOR DELIVERING AN ACTIVE SUBSTANCE FOR SUSTAINED RELEASE

[75] Inventors: Terrence B. Mazer, Reynoldsburg, Ohio; Glenn A. Meyer, Wankegan, Ill.; Shie-Ming Hwang, Arlington, Ohio; Edrick L. Candler, Jr., Dublin, Ohio; Lonnie R. Drayer, Gahanna, Ohio; Andre Daab-Krzykowski, Columbus, Ohio

[73] Assignee: Abbott Laboratories, Abbott Park, Ill.

[21] Appl. No.: 816,412

[22] Filed: Dec. 31, 1991

[51] Int. Cl.$^5$ .......................... A61K 9/26; A61K 9/14
[52] U.S. Cl. .................................... 424/469; 424/470; 424/491; 424/497
[58] Field of Search ............... 424/490, 499, 469, 470, 424/491, 497

[56] References Cited

U.S. PATENT DOCUMENTS

| | | | |
|---|---|---|---|
| Re. 32,307 | 12/1986 | Glatt et al. | 366/102 |
| 2,895,880 | 7/1959 | Rosenthal | 514/773 |
| 3,089,824 | 5/1963 | Wurster | 424/488 |
| 3,117,027 | 1/1964 | Lindolf et al. | 118/303 |
| 3,196,827 | 7/1965 | Wurster et al. | 118/24 |
| 3,241,520 | 3/1966 | Wurster et al. | 118/62 |
| 3,253,944 | 5/1966 | Wurster et al. | 427/213 |
| 3,558,768 | 1/1971 | Klippel | 434/494 |
| 3,802,896 | 4/1974 | Westall et al. | 523/100 |
| 3,939,259 | 2/1976 | Pescetti | 424/460 |
| 4,079,131 | 3/1978 | Lin et al. | 514/197 |
| 4,137,300 | 1/1979 | Sheth et al. | 424/460 |
| 4,308,251 | 12/1981 | Dunn et al. | 424/469 |
| 4,323,312 | 4/1982 | Glatt et al. | 366/102 |
| 4,384,004 | 5/1983 | Cea et al. | 426/3 |
| 4,525,339 | 6/1985 | Behl et al. | 424/459 |
| 4,844,910 | 7/1989 | Leslie et al. | 424/494 |
| 4,876,094 | 10/1989 | Benton et al. | 424/491 |
| 4,876,097 | 10/1989 | Autant et al. | 426/74 |
| 4,892,742 | 1/1990 | Shah | 424/480 |
| 4,895,725 | 1/1990 | Kantor et al. | 424/455 |
| 4,925,673 | 5/1990 | Steiner et al. | 424/455 |
| 4,943,449 | 7/1990 | Aishima et al. | 427/213.3 |
| 4,976,968 | 11/1990 | Steiner | 424/491 |
| 4,983,402 | 1/1991 | Steiner | 424/491 |
| 4,983,403 | 1/1991 | Ardaillon et al. | 436/2 |
| 5,066,436 | 11/1991 | Komen et al. | 264/4.3 |
| 5,068,112 | 11/1991 | Samejma et al. | 424/495 |
| 5,077,053 | 12/1991 | Kuncewitch | 424/441 |
| 5,085,868 | 2/1992 | Mattsson et al. | 424/490 |

FOREIGN PATENT DOCUMENTS

| | | |
|---|---|---|
| 103387 | 3/1984 | European Pat. Off. |
| 45-12759 | 5/1970 | Japan . |
| 61-141862 | 6/1986 | Japan . |
| 62-201823 | 9/1987 | Japan . |
| 3-988 | 1/1991 | Japan . |
| 935672 | 9/1963 | United Kingdom . |

OTHER PUBLICATIONS

Patent application Ser. No. 07/815,458 filed Dec. 31, 1991, T. Mazer, et al., "Prolamine Coatings for Taste-Masking Orally Administrative Medicaments".

"Pharmacokinetics and Bioavailability of a Controlled Release Amoxicillin Formulation", Arancibia et al., *International Journal of Clinical Pharmacology Therapy and Toxicology*, vol. 25, No. 2, (1987), pp. 97-100.

"Biopharmaceutical Evaluation of Sustained-Release Ethylcellulose Microcapsules Containing Amoxicillin Using Beagle Dogs", Uchida et al., *Chemical Pharmaceutical Bulletin*, vol. 37, No. 12, (1989), pp. 3416-3419.

*Primary Examiner*—Thurman K. Page
*Attorney, Agent, or Firm*—Lonnie R. Drayer; Donald O. Nickey

[57] ABSTRACT

A system for delivering an active substance has sustained release of the active substance in the intestinal tract. This delivery system is especially useful for an active substance such as a β-lactam antibiotic which preferably has minimal exposure to the acidic environment of the stomach. Particles comprise an active ingredient disposed in a core which has at least one coating of a prolamine and one coating of an enteric compound thereon. The particles may be very small and suspended in a liquid medium.

40 Claims, 10 Drawing Sheets

SYSTEM FOR DELIVERING AN ACTIVE SUBSTANCE FOR SUSTAINED RELEASE

The present invention relates generally to systems for sustained release of active substances in the digestive tract and more specifically to microcapsules in suspensions as a system for delivering an active substance for sustained release in the intestinal tract.

BACKGROUND OF THE INVENTION

Some medical conditions are best treated by administration of a pharmaceutical or other active substance which is formulated to allow the active substance or ingredient to act as quickly as possible. Such a formulation may comprise an injectable solution, suspension, or a readily dissolvable tablet or capsule. This type of formulation is useful, for instance, for treating acute pain, such as headaches, or pain associated with sudden trauma, such as an accident.

Other medical conditions are best treated by administration of a pharmaceutical or other active substance in such a way as to sustain its action over an extended period of time. This type of administration is useful, for example, for treating chronic pain, such as that associated with rheumatic or arthritic conditions, for the treatment of a chronic cardiovascular condition, or for administering an antibiotic in a course of treatment covering several days. Sustained action can be achieved by repeated administration of an immediate-release tablet or capsule at frequent intervals, for instance every four hours. However, this is generally inconvenient, especially during the night, when it is often necessary to awaken a patient to administer the suspension, tablet or capsule. In addition, such multiple dosing may lead to undesirable fluctuations in the plasma concentration of the active substance.

It has previously been proposed to produce a formulation which will release the active substance therein at a controlled rate such that the amount available in the body to treat the condition is maintained at a therapeutic level over an extended period of time. Particularly suitable periods are twelve hours and twenty-four hours, since such formulations need only be taken once or twice a day to maintain an effective treatment of the condition. Such formulations are generally known as "sustained-release formulations."

Many sustained-release formulations are already known, but there is no generally applicable method by which such formulations can be designed. Generally speaking, each sustained-released formulation is dependent on the particular active substance incorporated therein. In designing a formulation, it is generally necessary to take into account many factors, including the rates of absorption and clearance of the active substance, the interaction of the active substance with the excipients and/or coating to be used in the formulation, the solubility of the active substance and of the excipients and/or coatings, and the effects on the bioavailability of the active substance which may be caused by the excipient and/or coatings. It is, however, not possible to readily predict whether any particular formulation will provide the desired sustained-release, and it is generally found necessary to carry out considerable experimentation to produce a sustained-release formulation having the desired properties.

The challenge of providing a sustained release delivery system is greatly increased when the patient is an infant, young child, or a more mature person who is unable to easily ingest large tablets or capsules. Such persons are more amenable to the ingestion of pharmaceutical or other active substances via liquid suspensions. The challenge is increased exponentially when for such persons the active compound, which is to be delivered, such as a β-lactam antibiotic, is most effective when protected from acidic gastric juices and is desired to be gradually released in the intestine. These challenges are met by the system for delivery of an active substance which is disclosed herein.

DESCRIPTION OF THE PRIOR ART

The encapsulation of active substance is well known for a variety of purposes, among them to protect the active substance from degradation when in contact with other agents in a given product or composition; to modulate the release of the active substance, and to render the active substance capable of withstanding rigorous processing conditions during formulation into products.

Numerous prior art patents and publications address the objective of providing a sustained release formulation of an active substance in the gastrointestinal tract.

U.S. Pat. No. 4,525,339 teaches the desirability of protecting a β-lactam antibiotic from exposure to gastric juices, this being achieved by an enteric coating. One of the possible enteric coating materials suggested in this patent is zein. However; there is no suggestion of using zein in combination with another enteric coating. Furthermore, the data set forth below in the present document, (FIG. 1), indicates that zein is not a suitable material for use as an enteric coating unless an undesirably thick coating layer is used.

U.S. Pat. No. 4,079,131 teaches a liquid suspension for providing amoxicillin to a patient, but it does not address the issue of sustained release. The amoxicillin is suspended in an anhydrous vegetable oil vehicle containing a saccharide. However; an oil based suspension has taste characteristics which may severely impair the ease of administering amoxicillin to a young child. Additionally this patent does not address sustained release through use of a water based suspension.

Japanese Kokoku Sho 45-12759 teaches that a mixture of 90–99% zein and 1–20% HPMC (3–15% hydroxypropoxy group and 19–32% methoxy group) may be used to coat tablets for taste masking, but the resulting tablets are readily dissolved in gastric juice. This patent reference teaches that hydroxy propyl methyl cellulose must be mixed with zein to obtain taste masking properties.

"Pharmacokinetics and bioavailability of a controlled release amoxicillin formulation", Arancibia et al, *INTERNATIONAL JOURNAL OF CLINICAL PHARMACOLOGY THERAPY AND TOXICOLOGY*, Volume 25 No. 2, 1987, pages 97–100, reports the evaluation of an unsatisfactory sustained release system (which is not described) in an in vivo experiment. This article indicates that the sustained release system did, however, perform satisfactorily in in-vitro dissolution studies. "Biopharmaceutical Evaluation of Sustained-Release Ethylcellulose Microcapsules Containing Amoxicillin Using Beagle Dogs", Uchida et al., *CHEMICAL PHARMACEUTICAL BULLETIN*, Volume 37 No. 12, (1989), pages 3416–3419 shows that the desirability of a sustained-release amoxicillin has been recognized for some time, but this article does not address the desirability of delaying release of the amoxicillin until the drug is in the intestine.

U.S. Pat. Nos. 4,876,097 and 4,983,403 teach that zein may be used in a coating material that will release the core substance at pH's of ≦3.5, but will be stable in a pH of ≧5. These patents teach the use of such a delivery system for delivering an active substance to the second stomach of a ruminant, but do not address the issue of sustained release. However, the data presented in the present patent application does not support these pH ranges for the zein used in practicing the present invention.

Japanese Koka Sho 61-141862 teaches coating vitamin C cores with zein or shellac to obtain time release, but concludes that shellac is superior to zein for this purpose. The exact type of zein used in the experiments is not disclosed.

Japanese Kokoku Hei 3-988 teaches that a health food which is either inside of a gelatin capsule or coated with gelatin may advantageously be overcoated with a "high quality zein" to prevent the health food from being released until reaching the pylorus of the stomach. However, there is no teaching or indication that sustained release of the health food in the intestine is achievable with this method, or even is desirable. The main objective is to prevent the health food from being exposed in the mouth.

British Patent 935,672 (published Sep. 4,, 1963) teaches a "sustained release table" having an active substance dispersed in a matrix which contains zein. However, the structure disclosed in this patent gives a big initial release in gastric fluid, as opposed to the present invention, followed by a much slower release rate in intestinal fluid.

U.S. Pat. No. 3,558,768 teaches sustained release pharmaceutical compositions with a core of an active compound dispersed in a matrix which contains zein, with the core being coated with a layer of the active substance dispersed in a matrix containing a hydrophilic gum. The test data presented in this patent shows release of the active substance in gastric fluid to be substantially the same as in intestinal fluid.

U.S. Pat. No. 2,895,880 teaches that an active compound may be dispersed in a matrix containing zein in order to achieve time release of the active compound when orally ingested. However, there is no teaching or suggestion in this patent that release of the active compound in the stomach should be minimized. However, the data presented in the present application shows that a minimal release of an active substance in gastric juices is not achieved by such a structure.

European Patent Application 0130387 (published Mar. 21, 1984) teaches the use of a "lower level" of zein in the matrix of a tablet, and the zein is not used as a coating material. This tablet releases a large burst dosage in acid, followed by slower sustained release in a base. However, this is not the release pattern desired to be achieved in the present invention.

U.S. Pat. No. 4,892,742 teaches an active substance in a matrix which contains zein, and the core is coated with a "rate controlling polymer".

U.S. Pat. No. 3,802,896 teaches a coating solution which contains zein and has utility for taste masking, and possible sustained release, of an active substance. However, the use of only a single layer of this coating solution, no in combination with a layer of any other material, is disclosed in this patent.

U.S. Pat. No. 3,939,259 teaches a sustained release system of gelatin capsules containing: (a) uncoated particles of an active substance to be released in the stomach during the first hour after ingestion; (b) particles of the active substance coated with a mixture of zein and shellac to be released two hours after ingestion; and particles of the active substance with a thicker coating of the zein and shellac mixture which is to be released four hours after ingestion. This sustained release system is not designed to minimize release of the active ingredient in the stomach.

Japanese Kokai Sho 62-201823 teaches that beneficial bifido bacteria and lactic acid bacteria may be delivered to the intestine, and protected from exposure to gastric juices, by overcoating the capsule, or microcapsule, which contains the bacteria with zein. However, this structure readily underwent disintegration in intestinal juices within 3-12 minutes, which does not solve the problem of providing sustained release in the intestine.

U.S. Pat. No. 4,308,251 teaches a twice-a-day sustained release aspirin tablet having both a time release controlling agent, (preferably cellulose acetate phthalate, but could be zein), and an erosion promoting agent such as corn starch. However, there is no teaching or suggestion that an enteric coating should be used to minimize release of the aspirin in the stomach.

U.S. Pat. No. 4,137,300 teaches a sustained release dosage system having: (a) a core comprising an active substance and at least two members selected from the group consisting of a higher alkanol and alkanoic acid; and (b) a coating of a prolamine overlying the core. However; no time-release data is presented in this patent, and there is no teaching or suggestion to use an enteric coating in combination with the prolamine coating.

U.S. Pat. No. 4,876,094 teaches a controlled release liquid dosage formulation wherein a core of an active substance has a first coating of a fat which melts at less than 101° F., and is overcoated with cellulose acetate or zein. The carrier liquid has a pH of less than 5 and comprises a viscous solution of a sugar, preferably being a high fructose corn syrup.

The above noted and other known techniques have heretofore provided no solution for the development of a delivery system for active substances which remedies the aforenoted problems by permitting the sustained release of an active substance in the intestine with little or no release in the stomach.

DETAILED DESCRIPTION OF THE INVENTION

Figure 1:
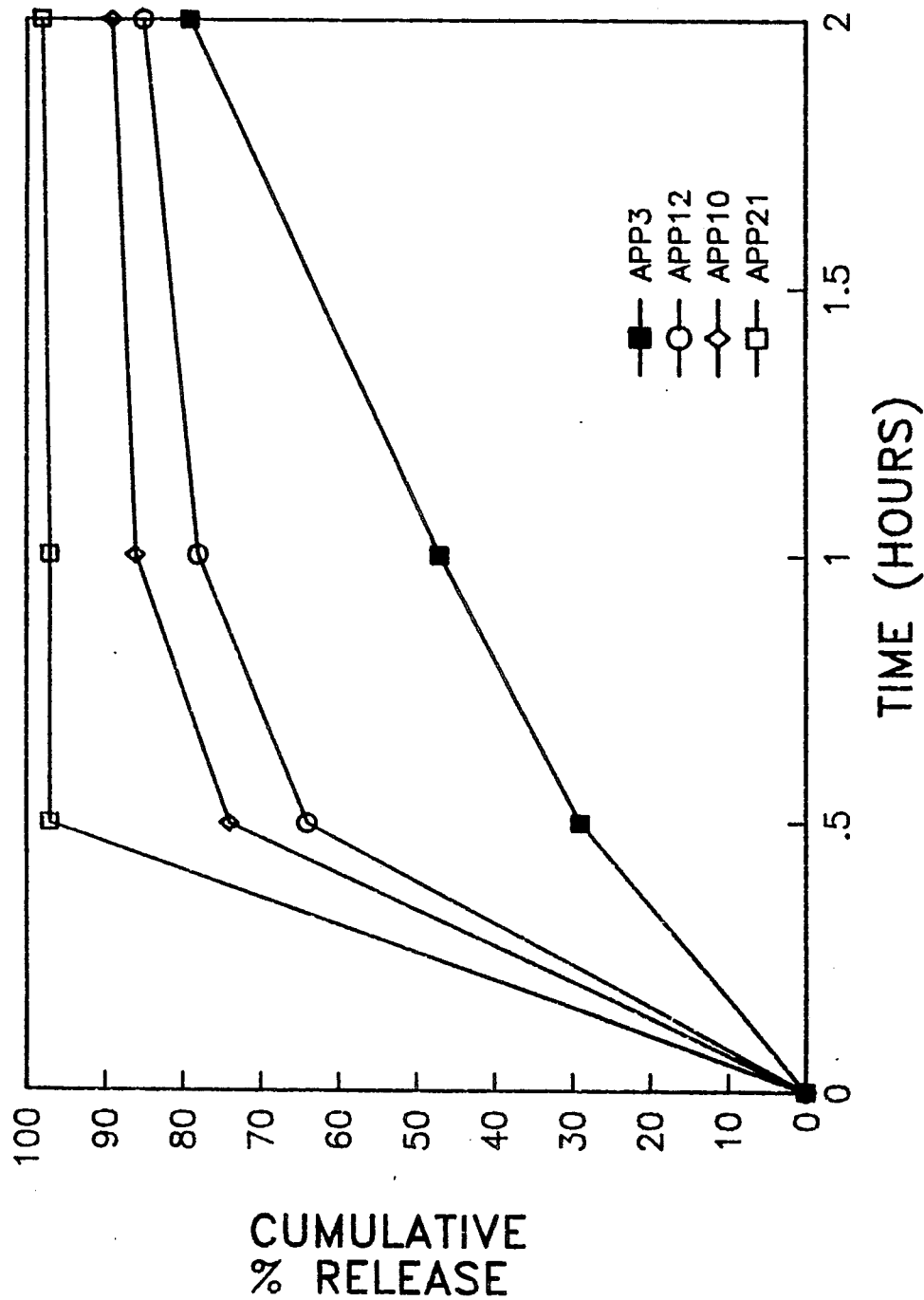
FIG. 1 is a graph showing the dissolution of acetaminophen from the cores of particles having a single zein coating thereon at a variety of weight percentages of the core, when the particles were placed in simulated gastric fluid at pH 1.2.

A delivery system for active substances is produced by a process which comprises forming the active compound and optionally one or more excipients and binders into a core, preferably using a rotor insert with fluid bed coating; applying a first coating to this core, preferably by fluid bed coating; applying a second coating over the particles thus formed, preferably by fluid bed coating. In some embodiments a third coating is then applied over the particles thus formed, preferably using fluid bed coating. It is preferable to screen the core particles initially formed before applying the first coating to enhance uniformity in the final product.

The active substance delivery system may be incorporated into a variety of pharmaceutical and nutritional products including pharmaceutical suspensions, pediatric infant nutritional formulas, and nutritional preparations. The present invention therefore encompasses pharmaceutical suspensions, pediatric infant formulas, and nutritional preparations, such as medical nutritionals for general health, as well as disease specific medical nutritionals, all incorporating the present active compound delivery system.

In accordance with the present invention, a delivery system for active substances is disclosed which comprises a composite particle structure having minimal dissolution in a suspension, minimal release in mouth and stomach of an active substance, and sustained release of the active substance in the intestinal tract. The present invention is a two or three coating layer encapsulation system for delivering an active substance to the intestine where the active substance will be slowly released.

A delivery system for an active substance in accordance with a first double coated embodiment of the invention generally comprises:
(a) a core comprising an active substance, or an active substance in a matrix with excipients;
(b) a first coating on the core comprising a prolamine in an amount from about 10% to about 70%, preferably about 20% to 50%, by weight of the total weight of the core; and,
(c) a second coating overlying the first coat and comprising at least one enteric compound in an amount from about 10% to about 70%, preferably about 20% to 60% by weight of the sum of the core material and the first coating.

A delivery system for an active substance in accordance with a second double coated embodiment of the invention generally comprises:
(a) a core comprising an active substance, or an active substance in a matrix with excipients;
(b) a first coating on the core comprising at least one enteric compound in an amount from about 10% to about 70%, preferably about 20% to 40% by weight of the total weight of the core; and,
(c) a second coating overlying the first coat and comprising a prolamine in an amount of from about 20% to 100%, preferably about 40% to 60%, by weight of the sum of the weights of the core and the first coating.

A delivery system for an active substance in accordance with a triple coated embodiment of with the present invention generally comprises:
(a) a core comprising an active substance, or an active substance in a matrix with excipients;
(b) a first coating comprising a prolamine in an amount from about 10% to about 70%, preferably about 10% to 30%, by weight of the total weight of the core;
(c) a second coating overlying the first coat and comprising at least one enteric compound in an amount from about 5% to about 70%, preferably about 20% to 40%, by weight of the sum of the total weights of the core and the first coating; and,
(d) a third coating comprising a prolamine in an amount of from about 22% to 100%, preferably about 40% to 70%, by weight of the sum of the weights of the core and the first two coatings.

Prolamines form the main protein components of cereal grains and flour. Unlike all other proteins, they can be extracted from flour with 80 percent alcohol, but they are insoluble in absolute alcohol and water. The most important prolamines are zein, gliadin, and hordein. Zein is preferred in the present invention.

As used herein and in the claims an "enteric compound" is understood to mean a composition of matter which is generally resistant to disintegration in human gastric fluids, but will disintegrate in human intestinal fluids, as well as compositions of matter which disintegrate very slowly in human gastric fluids, but more rapidly in human intestinal fluids.

The active substances which are believed to be suitable for incorporation in the core of an encapsulated particle in accordance with the present invention are bioactive substances including for example, analgesics, antibiotics, oncolytics, immunogens, antidepressants and other psychotherapy drugs, antivirals, drugs to treat HIV compromised individuals and individuals with AIDS, immuno-modulators, vitamins, dietary fiber and other nutrients, enzymes, hormones, vaccines, antibodies and other pharmaceuticals. The foregoing list is not intended to be inclusive but merely representative of various active compounds both simple and complex that are contemplated in accordance with the present invention.

A core containing an active substance(s) is prepared by standard processes such as spray drying, fluid bed coating, fluid bed coating with a rotor insert, and may optionally be prepared with additives such as excipients, including bulking agents, fillers, and binders. The excipients are generally present in amounts of up to 80% by weight of the total core material and can be mixed in combination with each other or used individually. Suitable excipients include, but are not limited to, carbohydrate materials, polyhydric alcohols, binders that are soluble at a pH greater than about 5.5, and mixtures thereof. Carbohydrates useful as excipients include traditional water-soluble sweetening agents such as monosaccharides, disaccharides and polysaccharides such as xylose, ribose, glucose, lactose, mannose, galactose, fructose, dextrose, sucrose, sugar, maltose, partially hydrolyzed starch, or corn syrup solids and sugar alcohols such as sorbitol, xylitol, mannitol and the like, and mixtures thereof. Suitable binders include for Example zein, polyvinylpyrrolidone, also known as PVP, methacrylic acid copolymer USP/NF Type A, methacrylic acid copolymer USP/NF Type B, methacrylic acid copolymer USP/NF Type C, blends of methacrylic acid copolymer USP/NF Type A and methacrylic acid copolymer USP/NF Type B, hydroxy propyl methyl cellulose phthalate, also known as HPMCP, HP50 or HP55, cellulose acetate phthalate, also known as C-A-P, cellulose acetate trimellitate, also known as C-A-T, blends of C-A-T and C-A-P, ethyl cellulose, and polyvinyl acetate phthalate, also known as PVAP. Gums, pectins, aligninates, mucilages, and mixtures thereof may also serve as suitable binders. Suitable binders in this group include gum arabic, tragacanth, karaya, ghattiagar, aliginates, carrageenans, fuercellaran, psyllium, and mixtures thereof.

Coating layers of the present invention which are not intended to have enteric characteristics comprise zein or other prolamines and a plasticizer or hydrophobic substance, or optionally, both a plasticizer and hydrophobic substance. The zein component for a non-enteric first coating layer preferably comprises zein with an ash content of 2% or less by weight. The method used to determine ash is in the USP XXII, "Residue on Ignition", sulfated. The zein used in many of the examples set forth herein was F 4000, manufactured by Freeman Industries, Tuckahoe, N.Y., U.S.A., with an ash content of about 1.1% by weight and zein F-400-LE from Freeman Industries with an ash content of about 0.07% by weight. The plasticizer may be generally selected from the group consisting of food grade glycols including triethylene glycol and propylene glycol, acetylated glycerides, oleic acid, lactic acid acetamide, ethylene glycol monooleate, glycerin, glyceryl monostearate, dibutyl tartrate, and tricresyl phosphate. A suitable hydrophobic substance used for the zein coating material comprises vegetable and animal fats, either unhydrogenated, hydrogenated, or partially hydrogenated, fatty acids, and glycerine esters of fatty acids, with representative materials comprising palm oil, palm kernel oil, soybean oil, rapeseed oil, rice bran oil, sunflower oil, safflower oil, coconut oil, castor oil, MCT oil, also known as glycerine ester of C6-C18 fatty acids derived from coconut oil, and mixtures thereof. Other hydrophobic substances also useful herein may be selected from monoglycerides, distilled monoglycerides, acetylated monoglycerides, diglycerides, triglycerides, and mixtures thereof. The hydrophobic substance used in the examples set forth herein for various zein coats was MCT oil, glycerine ester of C6-C18 fatty acids derived from coconut oil, manufactured by Karlshamns, of Columbus, Ohio, U.S.A., under the trade name Captex 355.

Materials suitable for use in the enteric coating layer include enteric coating substances, with representative materials comprising methacrylic acid copolymer USP/NF Type A (also known as Eudragit ® L 100, Eudragit ® L 12.5, and Eudragit ® L12.5P), methacrylic acid copolymer USP/NF Type B (also known as Eudragit ® S 100, Eudragit ® S 12.5P), blends of methacrylic acid copolymer USP/NF Type A and methacrylic acid copolymer USP/NF Type B, methacrylic acid USP/NF Type C (also known as Eudragit ® L 30D and Eudragit ® L 100-55), hydroxypropyl methylcellulose, hydroxy propyl methyl cellulose phthalate, also known as HPMCP, HP50 or HP55, cellulose acetate phthalate, also known as C-A-P, cellulose acetate trimellitate, also known as C-A-T, blends of C-A-T ad C-A-P, ,polyvinyl acetate phthalate, also known as PVAP, and ethyl cellulose, also known as EC. Eudragit ® is an acrylic copolymer based on methacrylic acid and methyl methacrylate from Rohm Pharmac, of Germany, which has as a U.S.A. agent Rohm Tech, Inc. of Malden, Mass. The foregoing examples are illustrative and not restrictive of suitable materials for inclusion in the delivery system of the invention, and the invention is considered to extend to unnamed equivalent materials within its scope. The enteric used herein was about a 3 to 1 weight/weight blend of Eudragit ® L 100 and Eudragit ® S 100, respectively, which is believed to be the best mode of practicing the invention.

A plasticizer component for the enteric coat component may comprise for example triethyl citrate, acetyltriethyl citrate, tri-n-butyl citrate, acetyltri-n-butyl citrate, dibutyl phthalate, diethyl phthalate, dibutyl sebacate, glyceryl triacetate, manufactured by Hoffman La Roche under the trade name of Triacetin ®, and acetylated monoglyceride, manufactured by Eastman Chemical Products under the trade name of Myvacet ® 9-45. The plasticizer used herein was triethyl citrate.

An anti-tackiness agent for the enteric coat component comprises talc, colloidal silca, and kaolin. The recommended level of anti-tackiness agents is preferably not greater than about 30% by weight of the total enteric compounds, in order to prevent the anti-tackiness agent from speeding disintegration of the enteric compound. The anti-tackiness agent used herein was Alpha-fil 500USP, talc manufactured by Cyprus Industrial Minerals Company, Englewood, Colo., U.S.A.

The preparation of the active compound delivery system may be accomplished by a variety of coating techniques known in the art including fluid bed coating, coascervation, or a combination thereof, and the like, as disclosed in U.S. Pat. No. 4,384,004 to Cea et. al. Preferably, fluid bed coating with a rotor insert may be employed to form the initial core, and fluid bed coating with a Wurster column may be employed to apply the first, second, and third coatings. In the fluidized bed procedure, with rotor insert, for preparing a core containing an active substance as employed herein, the active substance or active substance in a matrix is charged as a powder onto a variable speed horizontal rotor disc in an apparatus that creates a upward air current or stream in which the particles have a rotary movement about an at least approximately vertical axis. The particles pass through a zone of finely atomized coating material which causes the passing particles to be coated. Additional solvents can be applied after the application of the coating material to better form particles of the desired size. Finally, rotor speed is increased and fluidization air volume and air temperature are also increased to both form the particles and obtain the desired level of dryness. The foregoing method and apparatus are known as a fluidized bed with rotor disc and are set forth in detail in the following U.S. patents, the disclosures of which are incorporated herein by reference: U.S. Pat. Nos. 4,323,312 and Re.32,307.

In the fluidized bed with Wurster column procedure as applied herein for applying the various coatings, the cores produced with the fluidized bed with rotor insert described above, or other means, are suspended in an apparatus that creates a strong upward air current or stream in which the particles move. The stream passes through a zone of finely atomized coating material which causes the passing particles to be coated, after which the coated particles move upward through the Wurster column and then travel downward in a fluidized condition countercurrent to a flow of heated fluidized gas whereupon they are dried. The particles may reenter the upward stream for a further coating until the desired weight ratio of coating to active core has been obtained. The foregoing method and apparatus are known as the Wurster Process and are set forth in detail in the following U.S. patents, the disclosures of which are incorporated herein by reference: U.S. Pat. Nos. 3,089,824; 3,117,027; 3,196,827; 3,241,520; and 3,253,944.

The prolamine coating materials are prepared for use as a solution capable of being uniformly atomized. The solubility of zein requires a solvent with both polar and non-polar groups in the proper ratio. The proper ratio of polar and non-polar groups can be obtained with single solvents or two or more solvent mixtures. Examples of suitable single solvents are acetic acid, lactic acid, propionic acid, and propylene glycol. The aqueous alcohols are preferred as solvents in many applications. Examples of suitable alcohol/water systems are methanol/water, ethanol/water, isopropanol/water, and n-butanol/water. To obtain complete solubility above the cloud point, the ratio of alcohol to water varies for each alcohol chosen and the mixed solvent final temperature. If desired, other ingredients such as plasticizers or hydrophobic substances may be added to improve the properties of the final coating. Suitable plasticizers include triethylene glycol, propylene glycol, oleic acid, lactic acid acetamide, ethylene glycol monooleate, glycerin, glyceryl monostearate, dibutyl tartrate, and tricresyl phosphate. Suitable hydrophobic substances include vegetable and animal fats, either unhydrogenated, hydrogenated, or partially hydrogenated, fatty acids, and glycerine esters of fatty acids, with representative materials comprising palm oil, palm kernel oil, soybean oil, rapeseed oil, rice bran oil, sunflower oil, safflower oil, coconut oil, castor oil, MCT oil, also known as glycerine ester of $C_6-C_\sim$ fatty acids derived from coconut oil, and mixtures thereof. Other hydrophobic substances also useful herein may be selected from monoglycerides, distilled mono and diglycerides, acetylated mono and diglycerides, diglycerides, triglycerides, and mixtures thereof. The plasticizer may be added in known effective amounts within the scope of the invention. In general, amounts of about 5% to about 25% by weight of the zein are suitable.

The enteric coating is preferably applied to the core or coated particle using the technique described above. Plasticizers and anti-tackiness agents may be added to improve the properties of the coating. The plasticizer component for the enteric coat used in the practice of the present invention includes triethyl citrate, acetyltriethyl citrate, tri-n-butyl citrate, acetyltri-n-butyl citrate, dibutyl phthalate, diethyl phthalate, dibutyl sebacate, glyceryl triacetate, manufactured by Hoffman La Roche under the trade name of Triacetin ®, and acetylated monoglyceride, manufactured by Eastman Chemical Products, Kingsport, Tenn., U.S.A., under the trade name of Myvacet ® 9-45. The anti-tackiness agent for the enteric second coat component comprises talc, colloidal silca, and kaolin.

As used herein and in the claims when a coating component is stated as being as a percent of a particle, it should be understood that the coating component by itself is a weight percent of the particle including any prior coats. In the examples, all values of the weight percent of coating components were determined by analytical analysis. In addition to the stated weight percent of the coating component contained in the coat, the coat would also contain any specified plasticizer, hydrophobic substance, and anti-tackiness agent at the weight percent specified in the example.

EXAMPLE 1

Acetaminophen (APAP) is a well-known analgesic and antipyretic drug. In the United States, it is available for non-prescription over-the-counter sale in conventional liquid, suppository, capsule, tablet and caplet dosage forms. The tablet and caplet dosage forms typically contain 325 mg acetaminophen as "regular strength" or 500 mg as "extra strength". Normally, regular strength tablets or caplets are taken as one or two every four hours, and the extra strength tablet or caplets are taken as one or two every six hours. Ideally, it would be desirable to extend the dosing interval while maintaining the initial plasma concentrations achievable with conventional tablets or caplets. This would provide immediate and extended therapeutic analgesic or antipyretic effect and reduce the number of doses necessary, thereby making therapy more convenient.

Coated particles were prepared comprising acetaminophen from Mallinckrodt, Inc. St. Louis, Mo., U.S.A., as a core material coated with zein (F 4000) and then further coated with an enteric substance to form dual coated particles. The acetaminophen cores were prepared by sieving granular acetaminophen to a particle size range of about 177–420 microns. A solution of a coating material was prepared comprising zein (F 4000, Freeman Industries) plus MCT oil equaling 7.6% of the zein, as a 11.4% by weight solution of ethanol/water at a 80/20 weight/weight ratio. The acetaminophen cores were coated using a fluidized bed coating procedure in a 4"/6" fluid bed unit with a see-through main chamber, bottom spray, and Wurster column insert. The coating solution was applied to 500.0 grams of the acetaminophen cores at a rate that varied from about 6.7 to 7.5 grams/minute. Atomizing air pressure for the spray nozzle was about 25 PSIG. The fluidizing inlet air temperature varied automatically between 113° F. and 121° F. with a corresponding air discharge temperature of between 86° F. and 90° F. The resultant coated particles were sieved into particles in the range of about 420–500 microns, and particles larger than 500 microns. The 420–500 micron size particles were designated APP3, and had a coating of 73% by weight zein thereon. The particles having a size greater than 500 microns were designated APP4, and had a coating of 86% by weight zein thereon.

The 420–500 micron particle portion of the batch (APP4) was then subjected to a second fluidized bed coating procedure. A solution of a second coating material was prepared comprising Eudragit® L 100 and Eudragit® S 100, in a 3/1 weight/weight ratio, plus triethyl citrate equaling 15% by weight of the total Eudragit®, plus talc (Alpha-fil 500USP from Cyprus Industrial Minerals Company) equaling 30% by weight of the total Eudragit®, as a 12.0% by weight solution of ethanol/acetone at a 88.7/11.4 weight/weight ratio. The solution of the second coating material was then applied to 350 grams of the zein coated acetaminophen particles at a rate of about 7.6 grams/minute to form dually coated particles. Atomizing air pressure for the spray nozzle was about 16 PSIG. The fluidizing inlet air temperature automatically varied between 115° F. and 120° F. with a corresponding air outlet temperature between 86° and 93° F. The resultant dual coated particles were designated APP8 and comprised 73% by weight zein applied as a first coating, and 5% by weight Eudragit® as a second coating.

As a second product in this example, a coated particle was prepared comprising a core material of acetaminophen, coated with a mixture of Eudragit® RS 100 PM and Eudragit® RL 100 PM, in a 4/1 weight/weight ratio, respectively, and then further coated with zein (F 4000) to form a reverse dual coated product of the present invention. The acetaminophen was prepared by sieving granular acetaminophen to a particle size range of about 177–420 microns. The resulting particles were then coated by fluidized bed coating procedure in a 4"/6" fluid bed unit with a see-through main chamber, bottom spray, and Wurster column insert. Accordingly, a mixture of Eudragit® RS 100 PM and Eudragit® RL 100 PM, in a 4/1 weight/weight ratio, respectively, plus triethyl citrate equaling 6% by weight of the total Eudragit®, plus talc (Alpha-fil 500USP from Cyprus Industrial Minerals Company) equaling 15% by weight of the total Eudragit®, was prepared as a 12.0% by weight solution of ethanol/acetone at a 94.4/5.6 weight/weight ratio, and applied to 800 grams of acetaminophen granular particles. The Eudragit®/triethyl citrate/talc solution was applied at a rate of about 6.8 to 7.0 grams/minute. The fluid atomizing air pressure was about 16 PSIG. The fluidizing inlet air temperature automatically varied between 115° F. and 117° F. with a corresponding air outlet temperature between 87° F. and 90° F. Samples were taken and are designated APP6, which has 22% by weight total Eudragit® as Eudragit® RS 100 PM/Eudragit® RL 100 PM, 4/1 weight/weight ratio, respectively; and APP7, which has 35% by weight total Eudragit® as Eudragit® RS 100 PM/Eudragit® RL 100 PM, 4/1 weight/weight ratio, respectively.

The sample represented by APP7 was then subjected to a second fluid bed coating. Zein (F 4000, Freeman Industries) was then applied to 415 grams of the Eudragit® coated acetaminophen to form reverse dually coated particles, with Eudragit® next to the core as a first coat and zein on the outside as an exterior coating. Accordingly, zein (F 4000, Freeman Industries) plus MCT oil equaling 7.6% of the zein, was prepared as a 11.4% by weight solution of ethanol/water at a 80/20 weight/weight ratio. It was then applied to 415.0 grams of Eudragit® coated acetaminophen particles. The zein/MCT oil solution was applied at a rate of about 6.5 grams/minute. The fluidizing inlet air temperature varied automatically between 115° F. and 117° F. with a corresponding air discharge temperature of between 85° F. and 93° F. The batch was not sieved. A sample was taken and designated APP9, 35% by weight Eudragit® applied as a first coating, and then 75% by weight zein (F 4000) applied as a second coating.

The particles were subjected to dissolution tests in simulated gastric fluid (SGF) at pH 1.2 simulated intestinal fluid (SIF) at pH 6.8. The SGF and SIF were prepared per USP specs (USP XXII–NF XVII, pp. 1788–1789, 1990). Selected samples were also tested in SGF at pH 5.0, in pH 1.2 and 5.0 acids, and in pH 6.8 buffer. The pH 1.2 and 5.0 acids were prepared the same way as the corresponding SGF's, except no enzymes were added. Similarly, the pH 6.8 buffer was prepared the same way as the SIF, except no enzyme was added.

The dissolution test was conducted using apparatus 2 assembly, as specified by USP (USP XXII–NF XVII, pp. 1578–1579, 1990). The nominal capacity of the dissolution vessel was 1000 mL. A peddle was used as the stirring element at a rotational speed of 50 rpm. The temperature was maintained at 37°+0.5° C. using a circulating water bath.

The solution was sampled at 0.5, 1, and 2 hours for the test in SGF, and at 1, 3, and 6 hours for the test in SIF. A 10-mL aliquot was drawn at each sampling time through a 35 micron filter. The aliquot was then filtered again through a 0.45 micron filter for HPLC analysis to determine its drug content.

An HPLC method was developed for the determination of acetaminophen in zein-coated powders and in dissolution samples from various media. Zein-coated powders were dissolved in methanol for analysis. An acetaminophen USP reference standard was used for the quantitation. For zein-coated drug analysis, the standard was prepared in methanol. For dissolution sample analysis, the standard was prepared in water. Each sample or standard solution was then filtered through a 0.45 micron filter for HPLC analysis. A C-18 column connected with an UV detector at 244 nm was used for the HPLC analysis. The mobile phase was water/methanol (85/15, v/v) at a flow rate of 1.0 mL/min. The analysis time was 18–20 min/injection.

Dissolution results from the particles manufactured in Example 1 are set forth in Table 1.

TABLE 1

Dissolution Of Coated Acetaminophen In Simulated Gastric (pH 1.2) And Intestinal Fluids (pH 6.8)

| | | Cumulative % Release of APAP | | | | | |
|---|---|---|---|---|---|---|---|
| | | In SGF, pH 1.2 | | | In SIF, pH 6.8 | | |
| Sample | % Drug | 0.5 hr | 1 hr | 2 hr | 1 hr | 3 hr | 6 hr |
| APP3 | 55.9 | 29 | 47 | 79 | 24 | 44 | 67 |
| APP4 | 52.0 | — | — | — | 30 | 51 | 66 |
| APP6 | 75.8 | 64 | 86 | 101 | 83 | 91 | 102 |
| APP7 | 66.6 | 42 | 62 | 90 | 53 | 88 | 103 |
| APP8 | 52.2 | 3 | 7 | 20 | 24 | 44 | 73 |
| APP9 | 36.9 | 23 | 36 | 58 | 23 | 43 | 65 |

TABLE 1-continued

Dissolution Of Coated Acetaminophen In Simulated Gastric (pH 1.2) And Intestinal Fluids (pH 6.8)

| Sample | % Drug | Cumulative % Release of APAP | | | | | |
|---|---|---|---|---|---|---|---|
| | | In SGF, pH 1.2 | | | In SIF, pH 6.8 | | |
| | | 0.5 hr | 1 hr | 2 hr | 1 hr | 3 hr | 6 hr |
| APP21* | 100.0 | 97 | 97 | 98 | 98 | 101 | 102 |

*uncoated particles of Acetaminophen

The particles from sample APP9, which had a dual coating with the inner coat being an enteric compound and the exterior coating being a prolamine (zein), did exhibit sustained release, as compared to APP21 which is uncoated, in simulated intestinal fluid. Photomicrographs made of various structures from other of the Examples herein, after the zein coated particles were subjected to dissolution media showed that the zein did not totally disintegrate or dissolve, but remained in place throughout the dissolution. The photomicrographs in combination with the dissolution results from various particles, which will be discussed in later examples, indicate that the respective locations of the prolamine and enteric layers may be varied in order to facilitate the desired closing protocol for a given active substance to a particular patient population.

EXAMPLE 2

Dual coated particles were prepared using the same procedure as set forth in Example 1. In this instance, acetaminophen cores were prepared by sieving granular acetaminophen to a particle size range of about 177–420 microns. The first coating material was again zein (F 4000, Freeman Industries) and MCT oil, prepared as a 11.4% by weight solution of ethanol/water at a 80/20 weight/weight ratio, and applied to 800 grams of acetaminophen at a rate of about 6.2 grams/minute. Atomizing air pressure for the spray nozzle was about 18 PSIG. The fluidizing inlet air temperature initially varied automatically between 113° F. and 118° F. with a corresponding air discharge temperature of between 82° F. and 90° F. Because of high humidity, the fluidizing inlet air temperature was raised to between 164° F. and 165° F., with a corresponding air outlet temperature of between 97° F. and 113° F., in an attempt to control agglomeration. This increase in temperature appeared to be effective in reducing some of the agglomeration. Finally, in an attempt to further control agglomeration, the fluidizing inlet air temperature was again raised to between 166° F. and 173° F., with a corresponding air outlet temperature of between 103° F. and 111° F., that appeared to reduce agglomeration further. Preferably, the inlet air relative humidity is controlled to be less than 40%, if such a control is available on the equipment being used. The resultant particles were sieved and were designated: APP10, which comprised a coating of 22% by weight zein, with the particles having sizes of less than 500 microns; APP11, which comprised a coating of 24% by weight zein, with the particles having sizes of less than 500 microns; APP12, which comprised a coating of 31% by weight zein, with the particles having sizes of less than 500 microns; APP15, which comprised a coating of 34% by weight zein, with the particles having sizes of about 500–590 microns; APP16, which comprised a coating of 33% by weight zein with the particles having sizes in the range of about 500–590 microns; and APP17, which comprised a coating of 64% by weight zein, with the particles having sizes in the range of about 500–590 microns.

The particles represented by the sample designated APP12, were then subjected to a second fluidized bed coating procedure. A solution of a second coating material was prepared comprising a mixture of Eudragit ® L 100 and Eudragit ® S 100 in a 3/1 weight/weight ratio, plus triethyl citrate equaling 15% by weight of the toal Eudragit ®, plus talc (Alpha-fil 500USP from Cyprus Industrial Minerals Company) equaling 30% by weight of the total Eudragit ®, was prepared as a 12.0% by weight solution of ethanol/acetone at a 88.7/11.4 weight/weight ratio. The second coating material was then applied to 553 grams of the zein coated acetaminophen cores at a rate of about 6.4 grams/minute to form dually coated particles. Atomizing air pressure for the spray nozzle was about 16 PSIG. The fluidizing inlet air temperature automatically varied between 115° F. and 121° F. with a corresponding air outlet temperature between 85° F. and 87° F. At various times throughout the coating procedure samples were taken and sieved, and were designated: APP13, which comprised 31% by weight zein applied as a first coat followed by 18% by weight Eudragit ® as a second coat, with the particles having sizes of less than 500 microns; APP14, which comprises 31% by weight zein applied as a first coat followed by 30% by weight Eudragit ® as a second coat, with the particles having sizes of less than 500 microns; APP18, which designates 31% by weight zein as a first coat, followed by 39% by weight Eudragit ® as a second coat, with the particles having sizes in the range of about 500–590 microns; and APP19, which comprises 31% by weight zein applied as a first coat, followed by 56% by weight Eudragit ® as a second coat, with the particles having sizes in the range of about 500–590 microns.

The particles produced in this example were subjected to dissolution testing as described in Example 1, and the results are set forth in Table 2.

Selected samples were subjected to sequential dissolution. The sample was first in simulated gastric fluid (SGF) for 1 hour, and then in simulated intestinal fluid (SIF) for an additional 6 hours. Sampling time was at 0.5 and 1 hour in SGF and at 1, 3, and 6 hours in SIF.

Two methods were used for the sequential dissolution. In one method, a 40-mesh basket (USP apparatus 1 assembly) was used as the stirring element, in which the powder sample was placed. In the other method a paddle (USP apparatus 2 assembly) was used as the stirring element.

In the basket method, the dissolution medium was changed from SGF to SIF during the transition. In the paddle method, less SGF was initially used which was neutralized to pH 6.8 at the end of 1 hour. A prewarmed and more concentrated SIF solution was then added to make a SIF solution at the right concentration for the subsequent dissolution test. The paddle method was modified from an USP procedure for Delayed-release drugs (USP XXII-NF XVII, pp. 1580–1581, 1990).

TABLE 2

Dissolution Of Coated Acetaminophen In Simulated Gastric (pH 1.2) And Intestinal Fluids (pH 6.8)

| Sample | % Drug | Cumulative % Release of APAP | | | | | |
|---|---|---|---|---|---|---|---|
| | | In SGF, pH 1.2 | | | In SIF, pH 6.8 | | |
| | | 0.5 hr | 1 hr | 2 hr | 1 hr | 3 hr | 6 hr |
| APP10 | 80.7 | 74 | 86 | 89 | 70 | 84 | 88 |

TABLE 2-continued

Dissolution Of Coated Acetaminophen In Simulated Gastric (pH 1.2) And Intestinal Fluids (pH 6.8)

| Sample | % Drug | Cumulative % Release of APAP | | | | | |
|---|---|---|---|---|---|---|---|
| | | In SGF, pH 1.2 | | | In SIF, pH 6.8 | | |
| | | 0.5 hr | 1 hr | 2 hr | 1 hr | 3 hr | 6 hr |
| APP11 | 79.8 | 66 | 83 | 87 | 50 | 67 | 76 |
| APP12 | 75.1 | 64 | 78 | 85 | 51 | 65 | 73 |
| | | 50 | 70 | — | 76 | 79 | 79* |
| | | | | | 50 | 72 | 79** |
| APP13 | 59.5 | 9 | 11 | 17 | 33 | 67 | 78 |
| | | 4 | 6 | — | 36 | 58 | 71* |
| APP14 | 52.4 | 8 | 11 | 15 | 39 | 73 | 85 |
| | | 9 | 12 | — | 43 | 60 | 69* |
| APP15 | 73.4 | 40 | 68 | 85 | 33 | 63 | 85 |
| APP16 | 73.9 | 46 | 72 | 97 | 41 | 68 | 84 |
| APP17 | 59.3 | 27 | 46 | 74 | 25 | 44 | 68 |
| APP18 | 47.9 | 4 | 6 | 8 | 32 | 53 | 77 |
| APP19 | 41.3 | 3 | 4 | 6 | 24 | 56 | 76 |
| APP21 | 100.0 | 97 | 97 | 98 | 98 | 101 | 102*** |

*sequential dissolution procedure
**dissolution performed in pH 8.4 buffer
***uncoated particles of Acetaminophen The dissolution results for particles from samples APP3, APP10, APP12 and APP21 in simulated gastric fluid are presented in graphic form in FIG. 1. These samples were selected as being representative of the samples manufactured in Examples 1 and 2. The data for APP21 clearly demonstrates that uncoated particles of acetaminophen (APAP) are dissolved in gastric fluid very quickly. When the APAP cores were coated with a single layer of zein (APP3, APP10, APP12) the rate of dissolution of the APAP was slowed, but a majority of the APAP was released from the core within two hours. APP10, APP12, and APP3 had coating of 22%, 31% and 73%, respectively, zein as a weight percentage of the APAP core. Heavier coatings of zein slowed the release of the core material more than lighter coatings. However, it is an objective of the present invention to minimize the release of the active substance in the stomach, and coating the active substance with zein alone does not meet this objective. This objective is very significant when the active substance is one, such as a $\beta$-lactam antibiotic, which preferably has minimal contact with the acidic environment of the stomach. In consideration of the fact that the absorptive capacity of the stomach is only about 1% of the absorptive capacity of the intestinal tract, release of the active substance in the intestinal tract is very desirable if a rapid release of the active substance in the stomach is not indicated by the dosing protocol.

Figure 2:
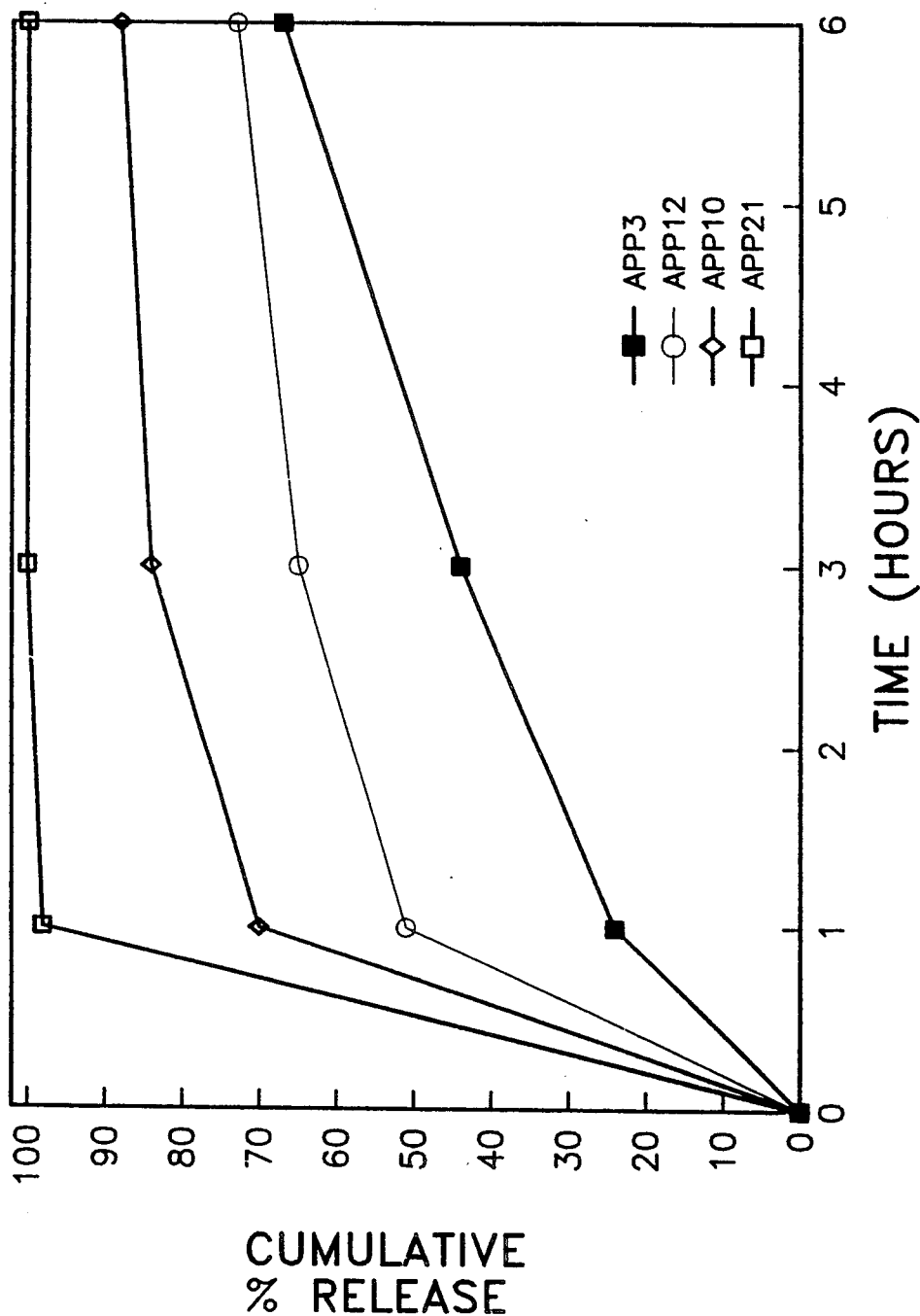
FIG. 2 is a graph showing the dissolution of acetaminophen from the cores of particles having a single zein coating thereon at various weight percentages of the core, when the particles were placed in simulated intestinal fluid at pH 6.8.

FIG. 2 is a graphic presentation of the dissolution rates of particles from samples APP3, APP10, APP12 and APP21 in simulated intestinal fluid. (These dissolutions were done with fresh particles, not those used in the dissolution results in simulated gastric fluid shown in FIG. 1.) Once again, the uncoated APAP particles (APP 21) were dissolved fairly rapidly. The particles coated with zein released the APAP from the cores much slower in a sustained release fashion. The particles having heavier coatings of zein on the cores had a more uniform sustained rate of release (APP3 as compared to APP10 and APP12). It is clear from this data that the quantity of the zein coating must be varied in order to achieve the desired rate of sustained release of an active substance in the intestinal tract.

It is interesting to note from Table 2 that particles from sample APP12 were also subjected to a sequential dissolution procedure, which confirmed that a majority of an active substance coated only with zein is released in the gastric fluid.

Figure 3:
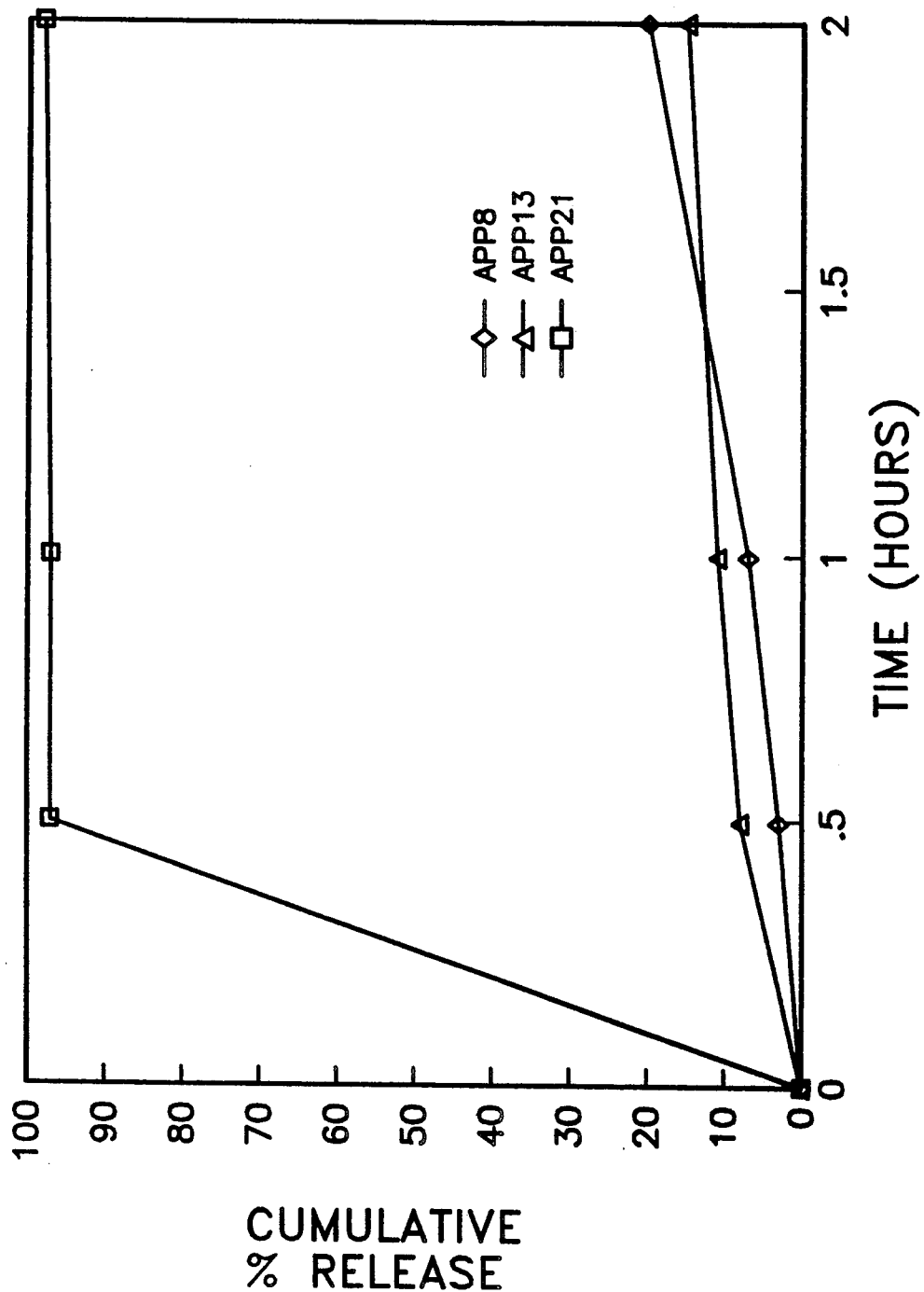
FIG. 3 is a graph showing the dissolution of acetaminophen from the cores of particles having a zein coating over the core, and an enteric coating over the zein coating, when the particles were placed in simulated gastric fluid at pH 1.2.

FIG. 3, when compared to FIG. 1, shows a significant reduction in the rate of dissolution of APAP when the cores are coated first with a layer of zein and then with a layer of an enteric substance. The APP8 particles are APP3 particles having an exterior layer of an enteric substance thereon, and the APP13 particles are APP12 particles having an exterior layer of an enteric substance thereon. As compared with the uncoated APAP particles (APP21) the enteric coated particles released a minimal amount of the active substance in the simulated gastric fluid.

Figure 4:
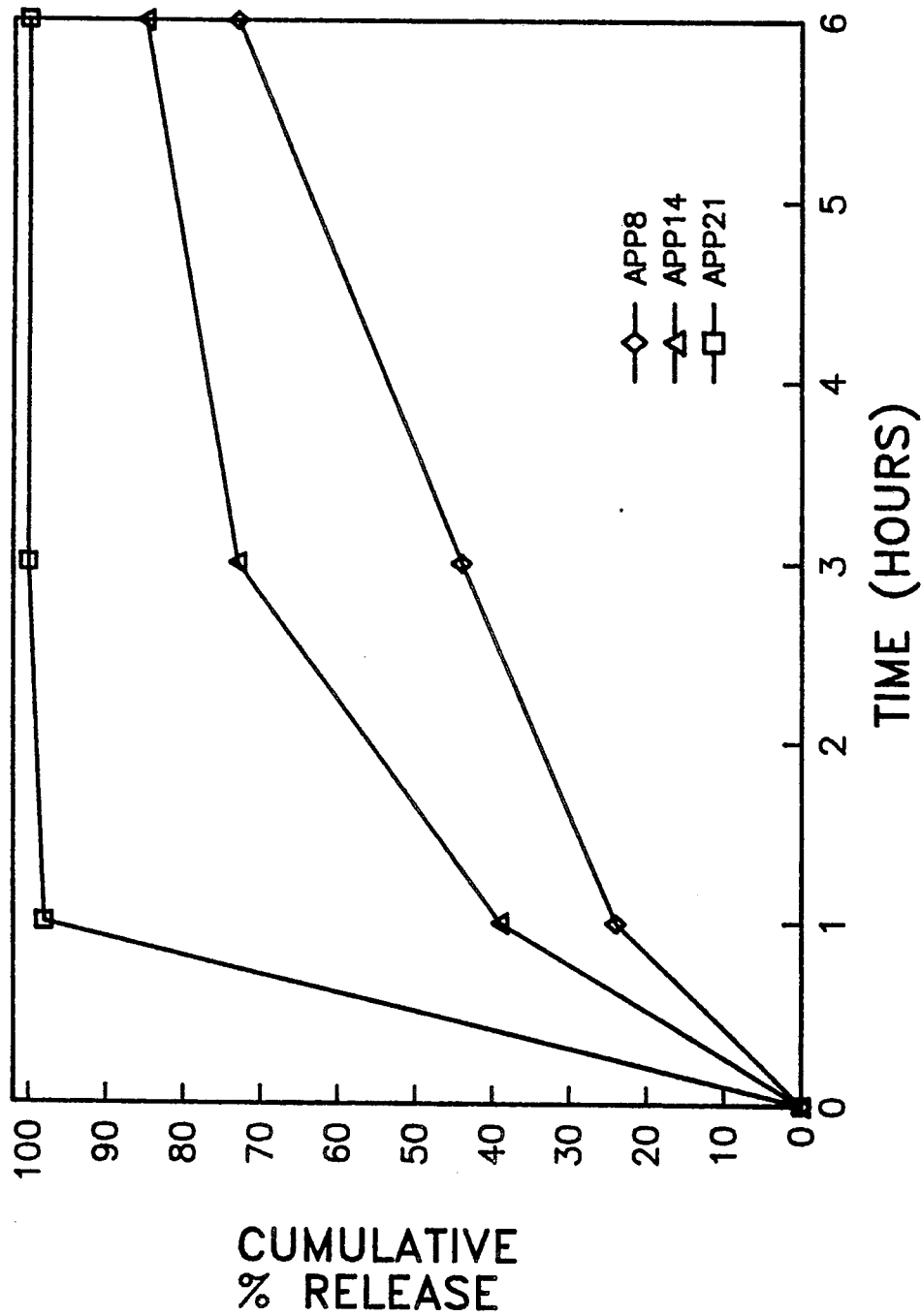
FIG. 4 is a graph showing the dissolution of acetaminophen from the cores of particles having a zein coating over the core and an enteric coating over the zein coating, when the particles were placed in simulated intestinal fluid at pH 6.8.

FIG. 4, when compared to FIG. 2, shows that the enteric coatings on particles from the same samples as shown in FIG. 3 did not significantly impair the sustained release characteristics in simulated intestinal fluid which are shown in FIG. 2.

It is to be noted from Table 2 that dual coated particles from sample APP13 were subjected to a sequential dissolution test which shows that dual coated particles of the type made in Example 2 do in fact restrict release of an active substance in simulated gastric fluid while exhibiting the desired sustained release characteristic in the simulated intestinal fluid.

It is believed that the dissolution rates of the APAP were affected by the fact that the APAP cores were elongated and needle-like in shape rather than spherical. This core shape resulted in thinner coatings at the "ends" of the cores, which affected dissolution results.

It may be fairly concluded from the data presented thus far that a composite structure for delivery of an active substance for sustained release in the intestinal tract in accordance with the present invention may comprise a core containing an active substance, said core being coated with a prolamine and said prolamine being coated with a layer of an enteric substance. It is understood that the amount of the coating materials is dependent upon the desired dosing protocol for the active substance.

EXAMPLE 3

Dual coated particles of the type prepared in Example 2 were further coated to form triple coated particles. In this instance, acetaminophen cores were prepared by sieving granular acetaminophen to particles having sizes in the range of about 125-250 microns. The first coating material was again zein (F 4000, Freeman Industries) and MCT oil; however, prepared as a 12% by weight solution of ethanol/water at a ratio of 87/13 weight/weight, and applied to 756 grams of acetaminophen at a rate of about 5.8 grams/minute. Atomizing air pressure for the spray nozzle was about 20 PSIG. The fluidizing inlet air temperature varied automatically between 155° F. and 170° F. with a corresponding air discharge temperature of between 108° F. and 117° F. A second batch of coated particles was prepared duplicating this procedure, and the two batches were intimately mixed in the fluid coating apparatus, after which additional zein coating was applied. At separate times during the coating procedure samples were taken, but not sieved and were designated: APP22, having a coating of 32% by weight zein applied; and APP23, having a coating of 46% by weight zein.

The particles designated APP23, were then subjected to a second fluidized bed coating procedure. A solution of a second coating material was prepared comprising a mixture of Eudragit ® L 100 and Eudragit ® S 100 in a 3/1 weight/weight ratio, plus triethyl citrate equaling 15% by weight of the total Eudragit ®, plus talc (Alpha-fil 500USP from Cyprus Industrial Minerals Company) equaling 30% by weight of the total Eudragit ®, as a 12.0% by weight solution of ethanol/acetone at a 88.7/11.4 weight/weight ratio. The solution of the second coating material was then applied to 846 grams of the zein coated acetaminophen particles at a rate that varied from about 5.5 to 6.0 grams/minute to form dually coated particles. The atomizing air pressure for the spray nozzle was about 16 PSIG. The fluidizing inlet air temperature was automatically varied between 118° F. and 126° F. with a corresponding air outlet temperature between 89° F. and 96° F. A sample was taken and sieved and was designated APP24, which comprised 46% by weight zein applied as a first coat, followed by 28% by weight Eudragit ® as a second coat, with the particles having sizes of less than 500 microns.

The particles designated APP≧ were split in two batches. One of those batches was subjected to a third fluidized bed coating procedure. A solution of a third coating material was prepared comprising zein (F 4000, Freeman Industries) and MCT oil; as a 12% by weight solution of ethanol/water at a ratio of 87/13 weight/weight. The solution of the third coating material was applied to 374 grams of the APP24 particles at a rate of about 5.4 to 6.5 grams/minute. The atomizing air pressure for the spray nozzle was about 18 PSIG. The fluidizing inlet air temperature varied automatically between 168° F. and 173° F. with a corresponding air discharge temperature of between 106° F. and 117° F. At various times throughout the coating procedure samples were taken, sieved, and designated as follows: APP25, which comprises 46% by weight zein (F 4000) applied as a first coat followed by 28% by weight Eudragit ® as a second coat followed by 23% zein (F 4000) as a third coat, with the particles having sizes of less than 500 microns; APP26, which comprised 46% by weight zein (F 4000) applied as a first coat followed by 28% by weight Eudragit ® as a second coat followed by 7% zein (F 4000) applied as a third coat, with the particles having sizes of less than 297 microns; and APP27, which designates 46% by weight zein (F 4000) as a first coat followed by 28% by weight Eudragit ® as a second coat followed by 41% zein (F 4000) as a third coat, with the particles having sizes in the range of about 297–420 microns.

The other batch of particles from the sample designated APP24, was then subjected to a third fluidized bed coating procedure. A solution of a third coating material was prepared comprising a different zein (F 4000LE, Freeman Industries) and MCT oil, prepared as a 12% by weight solution of ethanol/water at a ratio of 87/13 weight/weight, and applied to 338 grams of the APP24 particles at a rate of about 5.2 to 5.7 grams/minute. Atomizing air pressure for the spray nozzle was about 18 PSIG. The fluidizing inlet air temperature varied automatically between 168° F. and 173° F. with a corresponding air discharge temperature of between 106° F. and 114° F. At various times throughout the coating procedure samples were taken, sieved, and designated as follows: APP30, which comprised 46% by weight zein (F 4000) applied as a first coat followed by 28% by weight Eudragit ® as a second coat followed by 18% by weight zein (F 4000LE) as a third coat, with the particles having sizes of less than 420 microns; and APP32, which comprised 46% by weight zein (F 4000) applied as a first coat followed by 28% by weight Eudragit ® as a second coat followed by 28% zein (F 4000 LE) applied as a third coat, with the particles having sizes of less than 420 microns.

The particles manufactured in this example were then subjected to dissolution testing as described in Example 1. Selected particle samples were subjected to sequential dissolution testing as described in Example 2. The results of these dissolution tests are set forth in Table 3.

TABLE 3

Dissolution Of Coated Acetaminophen In Simulated Gastric (pH 1.2) And Intestinal Fluids (pH 6.8)

| Sample | % Drug | Cumulative % Release of APAP | | | | | |
|---|---|---|---|---|---|---|---|
| | | In SGF, pH 1.2 | | | In SIF, pH 6.8 | | |
| | | 0.5 hr | 1 hr | 2 hr | 1 hr | 3 hr | 6 hr |
| APP21 | 100.0 | 97 | 97 | 98 | 98 | 101 | 102 |
| APP22 | 74.1 | 65 | 90 | 97 | 42 | 78 | 90 |
| APP23 | 66.7 | 63 | 87 | 98 | 26 | 51 | 65 |
| | | 62 | 88 | — | 96 | 94 | 94* |
| APP24 | 47.8 | 6 | 10 | 18 | 47 | 88 | 104 |
| | | 6 | 11 | — | 36 | 54 | 63* |
| APP25 | 38.2 | 11 | 16 | 23 | 26 | 60 | 80 |
| APP26 | 44.4 | 15 | 23 | 34 | 33 | 67 | 82 |
| APP27 | 32.9 | 11 | 15 | 24 | 17 | 35 | 55 |
| | | 11 | 15 | — | 41 | 78 | 93* |
| APP30 | 40.0 | 7 | 10 | 18 | 12 | 33 | 55 |
| APP32 | 36.5 | 11 | 16 | 26 | 21 | 41 | 57 |
| | | 9 | 14 | — | 32 | 50 | 66* |

*sequential dissolution procedure

Figure 5:
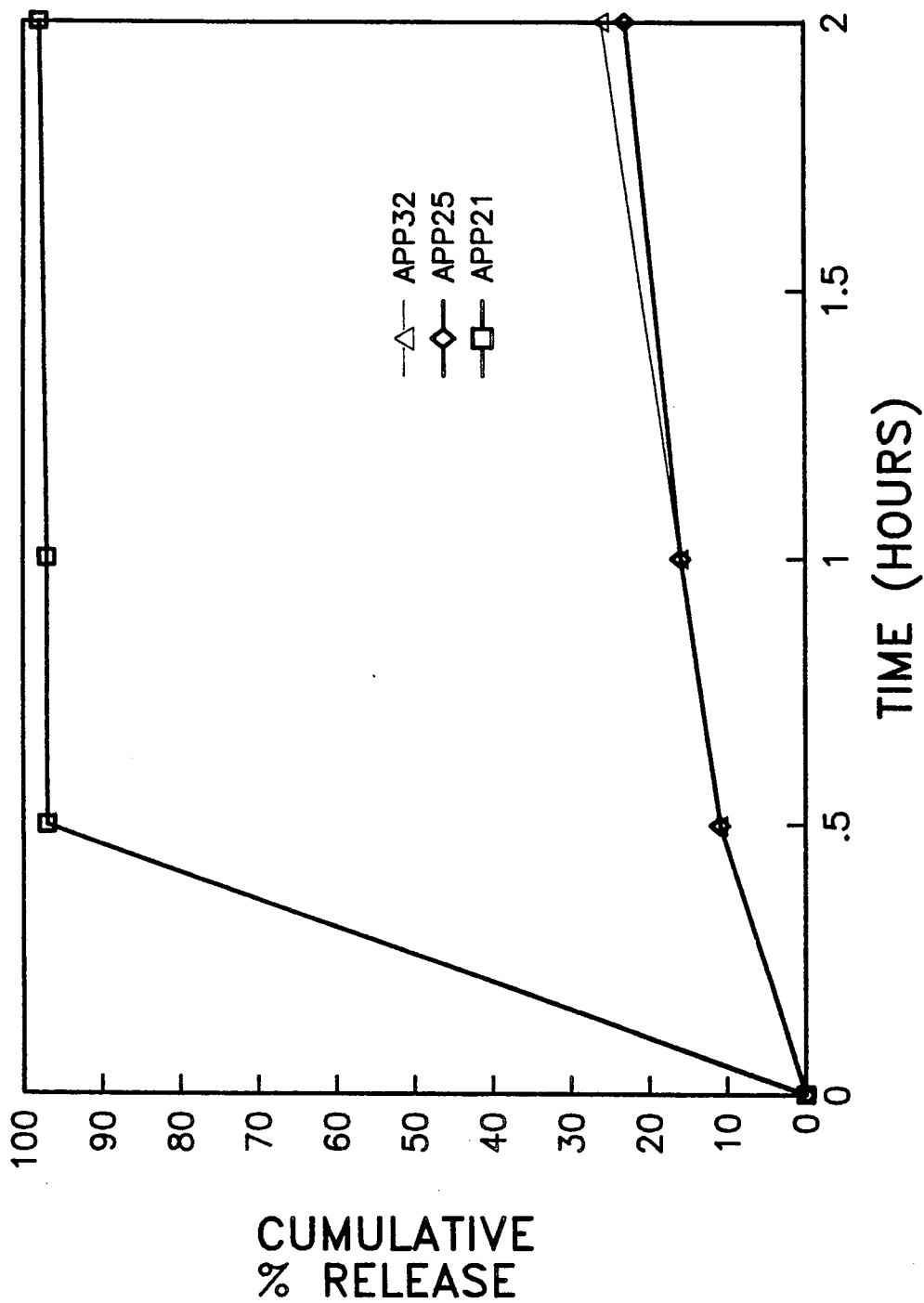
FIG. 5 is a graph showing the dissolution of acetaminophen from the cores of particles having a first zein coating over the core, with an enteric coating over the first zein coating, followed by a second coating of zein over the enteric coating, the particles were placed in simulated gastric fluid at pH 1.2.
Figure 6:
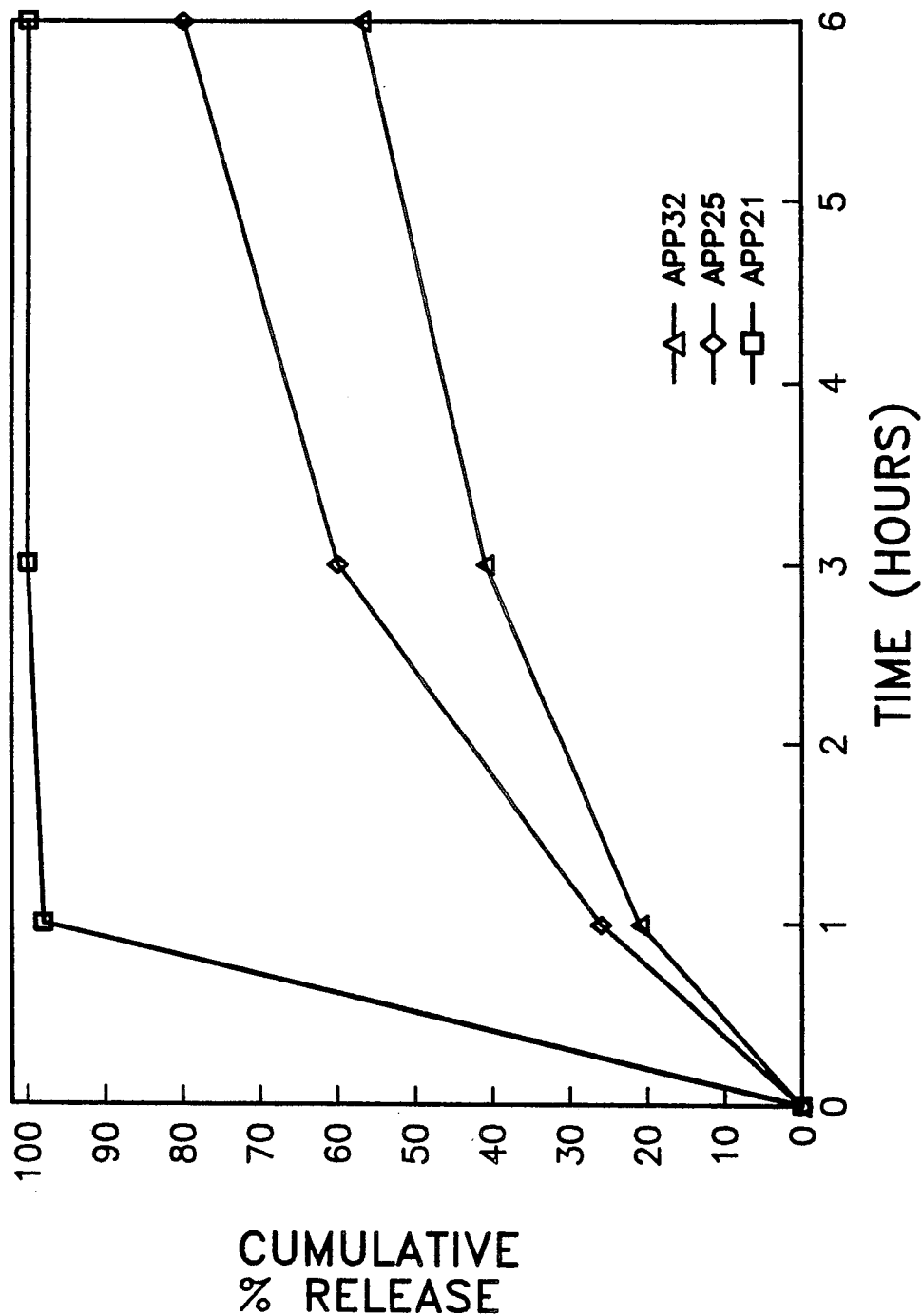
FIG. 6 is a graph showing the dissolution of acetaminophen from the cores of particles having a first zein coating over the core, with an enteric coating over the first zein coating, followed by a second coating of zein over the enteric coating, when the particles were placed in simulated intestinal fluid at pH 6.8.

FIGS. 5 and 6 are graphs showing the dissolution of triple coated particles manufactured in Example 3 in simulated gastric fluid and simulated intestinal fluid, respectively. In both of these graphs APP21 represents the dissolution of uncoated particles of acetaminophen (APAP). Particles from samples APP25 and APP32 have a first coating layer of zein on an APAP core, then a layer of an enteric substance over the first zein layer, and then a second coating of a zein as an exterior coating on the particles. The desirability of an exterior coating of zein will be better explained in Example 11 wherein such particles are placed in liquid suspensions. At this point it can be briefly stated that an exterior coating of zein will protect the enteric coating when the particles are placed in a liquid medium having a pH of greater than about 5.0. When FIG. 5 is compared to FIG. 3 it is clear that an exterior coating of zein does not significantly impair the property of the enteric coating for minimizing the release of an active substance from the core in simulated gastric fluid. Furthermore, when FIG. 6 is compared to FIG. 4, it is clear that the exterior coating of zein does not significantly impair the desired sustained release of the active substance in simulated intestinal fluid, although the rate of release may be slowed.

Figure 7:
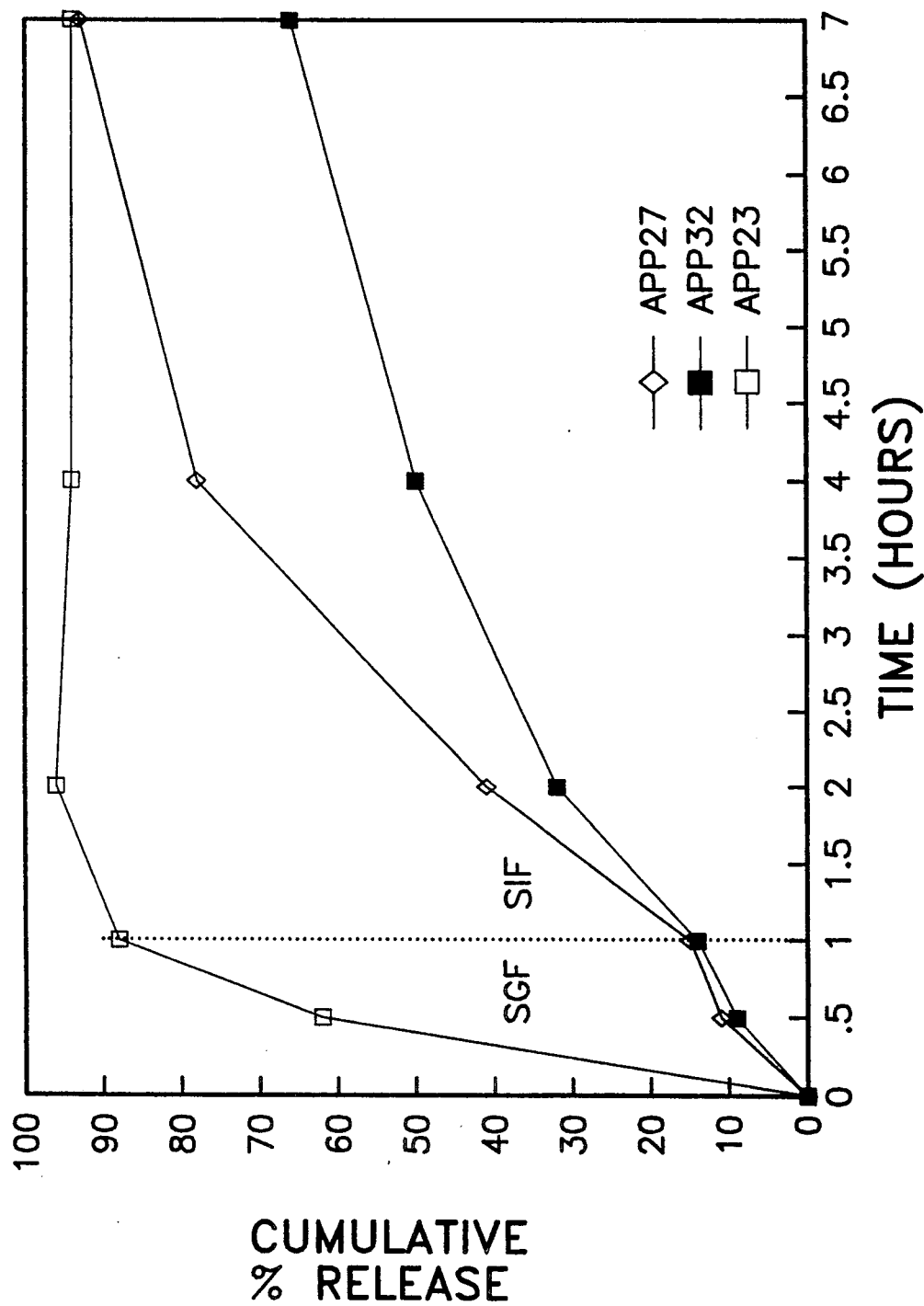
FIG. 7 is a graph showing the dissolution of acetaminophen from the cores of particles having a first zein coating over the core, with an enteric coating over the first zein coating, followed by a second coating of zein over the enteric coating, when the particles were sequentially placed in simulated gastric fluid at pH 1.2 for one hour, followed by placement in simulated intestinal fluid at pH 6.8 for six hours.

FIG. 7 is a graphic representation of the dissolution of an active substance (APAP) when triple coated particles (APP27 and APP32) are subjected to the sequential dissolution procedure as compared to particles having only a single coating of zein on the core (APP23). It can be concluded from this data that the triple coated particles exhibit a minimal rate of release in the simulated gastric fluid followed by the desired sustained rate of release in simulated intestinal fluid. The outer coating on the APP32 particles is a zein having a lower ash content than that in the outer coating of the APP27 particles. This data indicates that a slower rate of sustained release is attained when a zein having a lower ash content is used in coating the particles.

EXAMPLE 4

In this example, single coated particles were prepared comprising a core material of acetaminophen, coated with zein (F 4000), varying the level of the hydrophobic substance, MCT oil, and also substituting plasticizers at different levels for the MCT oil. In this example, acetaminophen cores were prepared by sieving granular acetaminophen to a particle size range of about 125–297 microns.

A solution of a coating was prepared comprising zein (F 4000, Freeman Industries) and MCT oil, which is a hydrophobic plasticizer, at 7.6% by weight of the zein; as a 25% by weight solution of ethanol/water at a ratio of 87/13 weight/weight. The solution of the coating material was applied to 750 grams of the acetaminophen cores at a rate between 5.3–11.4 grams/minute. The atomizing air pressure for the spray nozzle was about 14 PSIG. The fluidizing inlet air temperature varied automatically between 137° F. and 150° F. with a corresponding air discharge temperature of between 91° F. and 100° F. A sample was taken and sieved, and was designated APP36, which comprised a coating of 37% by weight zein (F 4000) with the particles having sizes of less than 297 microns.

A solution of a coating material was prepared comprising zein (F 4000, Freeman Industries) and MCT oil at 5% by weight of the zein, as a 24.6% by weight solution of ethanol/water at a ratio of 87/13 weight/weight, and was applied to 750 grams of acetaminophen cores at a rate between 6.0–6.3 grams/minute. The atomizing air pressure for the spray nozzle was about 14 PSIG. The fluidizing inlet air temperature varied automatically between 133° F. and 142° F. with a corresponding air discharge temperature of between 95° F. and 101° F. A sample was taken and sieved, and was designated APP35, which comprised a coating of 44% by weight zein (F 4000) with the particles having sizes of less than 297 microns.

A solution of a coating material was prepared comprising zein (F 4000, Freeman Industries) and MCT oil at 20% by weight of the zein; prepared as a 25.0% by weight solution of ethanol/water at a ratio of 87/13 weight/weight; and was applied to 750 grams of acetaminophen cores at a rate between 6.0–6.1 grams/minute. The atomizing air pressure for the spray nozzle was about 14 PSIG. The fluidizing inlet air temperature varied automatically between 131° F. and 143° F. with a corresponding air discharge temperature of between 88° F. and 101° F. Less plugging of the fluid nozzle occurred than at the lower levels of MCT oil; however, particle agglomeration appeared equivalent, again likely due to the 25.0% by weight solution being too high. A sample was taken and sieved, and was designated APP37, which comprised a coating of 41% by weight zein (F 4000) with the particles having sizes of less than 297 microns.

A fourth batch of particles was prepared using a combination of Myvacet ® 9-45 and Myverol ® P-06, which are amphoteric substances, in a 4/1 weight/weight ratio at 7.6% by weight of the zein, as a replacement for the MCT oil. Both Myvacet ® 9-45 and Myverol ® P-06 are products manufactured by Eastman Chemicals. A solution of a coating material was prepared comprising zein (F 4000, Freeman Industries) and a combination of Myvacet ® 9-45 and Myverol ® PO-6 in a 4/1 weight/weight ratio at 7.6% by weight of the zein, as a 25.0% by weight solution of methanol/acetone/water at a ratio of 82/14/4 weight/weight/weight, and was applied to 750 grams of acetaminophen at a rate between 6.6–6.8 grams/minute. The atomizing air pressure for the spray nozzle was about 14 PSIG. The fluidizing inlet air temperature varied automatically between 126° F. and 133° F. with a corresponding air discharge temperature of between 88° F. and 96° F. A sample was taken and sieved, and was designated APP38, which comprised a coating of 45% by weight zein (F 4000) with the particles having sizes of less than 297 microns.

A fifth batch of particles was prepared using a combination of Myvacet ® 9-45 and Myverol ® P-06, in a 4/1 weight/weight ratio at 20.0% by weight of the zein, as a replacement for the MCT oil. A solution of a coating material was prepared comprising zein (F 4000, Freeman Industries) and a combination of Myvacet ® 9-45 and Myverol ® P-06 in a 4/1 weight/weight ratio at 20% by weight of the zein, as a 24.2% by weight solution of methanol/acetone/water at a ratio of 82/14/4 weight/weight/weight, and was applied to 750 grams of acetaminophen at a rate of between 6.2–8.9 grams/minute. The atomizing air pressure for the spray nozzle was about 12 PSIG. The fluidizing inlet air temperature varied automatically between 128° F. and 141° F. with a corresponding air discharge temperature of between 89° F. and 96° F. A sample was taken and sieved, and was designated APP39, which comprised coating of 46% by weight zein (F 4000) with the particles having sizes of less than 297 microns.

The particles produced in this example were subjected to dissolution testing as described in Example 1. The results of these dissolution tests are set forth in Table 4.

TABLE 4

| | Dissolution Of Coated Acetaminophen In Simulated Gastric (pH 1.2) And Intestinal Fluids (pH 6.8) | | | | | | | | |
|---|---|---|---|---|---|---|---|---|---|
| | | | | Cumulative % Release of APAP | | | | | |
| | | Plasticizer | | In SGF, pH 1.2 | | | In SIF, pH 6.8 | | |
| Sample | % Drug | Hydrophobic | Amphoteric | 0.5 hr | 1 hr | 2 hr | 1 hr | 3 hr | 6 hr |
| APP21* | 100. | — | — | 97 | 97 | 98 | 98 | 101 | 102 |
| APP35 | 68.4 | 5% | — | 72 | 95 | 99 | 70 | 98 | 103 |
| APP36 | 71.8 | 7.6% | — | 69 | 92 | 98 | 72 | 91 | 93 |
| APP37 | 66.9 | 20% | — | 61 | 89 | 100 | 60 | 87 | 96 |
| APP38 | 67.5 | — | 7.6% | 71 | 97 | 99 | 66 | 94 | 100 |
| APP39 | 64.2 | — | 20% | 68 | 96 | 102 | 65 | 95 | 103 |

*uncoated APAP

In all of these samples an attempt was made to have a substantially constant level of zein applied as 37–46% of the weight of the core, with the hydrophobic substance and levels varying, or substituting an amphoteric plasticizer for the hydrophobic substance. A first conclusion is that the rate of release initially decreased in both SGF and SIF with increasing levels of MCT oil, however this effect is modest and becomes almost non-apparent in both SGF and SIF over a period of time, and that the differences are not significant. There appears to be no significant difference if plasticizer is substituted for MCT oil.

To prevent pure zein from cracking, the zein needs to be mixed with a plasticizer or hydrophobic, and these can interchangeably be used. However, if there is a critical active substance for which leakage needs to be restricted as much as possible the MCT oil or the hydrophobic substance is preferred.

EXAMPLE 5

In this example, triple coated particles, of the type manufactured in Example 3, were manufactured. In this example the effect of zein with two different levels of ash content was evaluated in various coating layers, "Zein LE" designates zein from Freeman Industries having an ash content equal to or less than 0.1%, and "Zein" is also from Freeman Industries and has an ash content of up to 2%. In this instance, a granular acetaminophen with a particle size range of about 125–250 microns was used for the cores. No further sieving was performed. The first coating material was again zein (F 4000, Freeman Industries) and MCT oil; however, prepared as a 20% by weight solution of ethanol/water at a ratio of 87/13 weight/weight. The first coating solution was applied to 800 grams of acetaminophen at a rate of about 3.2–4.9 grams/minute. The atomizing air pressure for the spray nozzle was about 14 PSIG. The fluidizing inlet air temperature varied automatically between 137° F. and 143° F. with a corresponding air discharge temperature of between 95° F. and 110° F. Minimum agglomeration and no nozzle plugging occurred. A sample taken, but not sieved, was designated APP40, which comprised a single coating of 23% by weight zein (F 4000) applied to the core.

Particles from the sample designated APP40, were then subjected to a second fluidized bed coating procedure. A solution of a second coating material was prepared comprising a mixture of Eudragit ® L 100 and Eudragit ® S100 in a 3/1 weight/weight ratio, plus triethyl citrate equaling 15% by weight of the total Eudragit ®, plus talc (Alpha-fil 500USP from Cyprus Industrial Minerals Company) equaling 30% by weight of the total Eudragit ®, as a 10.7% by weight solution of ethanol/acetone/water at a 87.0./10.0/3.0 weight-/weight/weight ratio. This second coating material was then applied to 500 grams of the APP40 particles at a rate of about 5.0 grams/minute to form dually coated particles. The atomizing air pressure for the spray nozzle was about 16 PSIG. The fluidizing inlet air temperature automatically varied between 105° F. and 132° F. with a corresponding air outlet temperature between 86° F. and 93° F. Minimum agglomeration and no nozzle plugging occurred. A sample was taken, but not sieved, and was designated APP41, which comprised 23% by weight zein (F 4000) applied as a first coat followed by 19% by weight Eudragit ® as a second coat.

Particles from the sample designated APP41 were then subjected to a third fluidized bed coating procedure. A solution of a third coating material was prepared comprising zein (F 4000LE, Freeman Industries) and MCT oil at 7.6% by weight of the zein; as a 20% by weight solution of ethanol/water at a ratio of 87/13 weight/weight. The solution of the third coating material was applied to 500 grams of the APP41 particles at a rate of about 5.3 to 5.4 grams/minute. The atomizing air pressure for the spray nozzle was about 14–20 PSIG. The fluidizing inlet air temperature varied automatically between 128° F. and 146° F. with a corresponding air discharge temperature of between 94° F. and 103° F. A sample was taken and sieved and was designated APP42, which comprised 23% by weight zein (F 4000) applied as a first coat followed by 19% by weight Eudragit ® as a second coat followed by 23% by weight zein (F 4000LE) as a third coat, with the particles having a size of less than 297 microns.

A second batch of particles was then prepared, again using the granular acetaminophen comprising particles having sizes in the range of about 125–250 microns as cores. A solution of a first coating material was prepared comprising zein (F 4000LE), Freeman Industries) and MCT oil at 7.6% by weight of the zein; as a 20% by weight solution of ethanol/water at a ratio of 87/13 weight/weight. The solution of the first coating material was applied to 800 grams of acetaminophen cores at a rate of about 5.3 grams/minute. The atomizing air pressure for the spray nozzle was about 14 PSIG. The fluidizing inlet air temperature varied automatically between 139° F. and 142° F. with a corresponding air discharge temperature of between 95° F. and 109° F. Minimum agglomeration and no nozzle plugging occurred. A sample was taken, but not sieved, and was designated APP44, comprising a single coating of 20% by weight zein (F 4000LE).

Particles from the sample designated APP44, were then subjected to a second fluidized bed coating procedure. A solution of a second coating material was prepared comprising a mixture of Eudragit ® L 100 and Eudragit ® S 100 in a 3/1 weight/weight ratio, plus triethyl citrate equaling 15% by weight of the total Eudragit ®, plus talc (Alpha-fil 500USP from Cyprus Industrial Minerals Company) equaling 30% by weight of the total Eudragit ®, as a 10.7% by weight solution of ethanol/acetone/water at a 87.0./10.0/3.0 weight-/weight/weight ratio. The solution of the second coating material was then applied to 490 grams of the APP44 particles to form dually coated particles at a rate of about 4.9–5.0 grams/minute. The atomizing air pressure for the spray nozzle was about 16 PSIG. The fluidizing inlet air temperature automatically varied between 114° F. and 115° F. with a corresponding air outlet temperature between 84° F. and 93° F. Minimum agglomeration and no nozzle plugging occurred. A sample were taken but not sieved and was designated APP45, which comprised 20% by weight zein (F 4000LE) applied as a first coat, followed by 16% by weight Eudragit ® as a second coat.

Particles represented by the sample designated APP45 were subjected to a third fluidized bed coating procedure. A solution of a third coating material was prepared comprising zein (F 4000LE, Freeman Industries) and MCT oil at 7.6% by weight of the zein; as a 20% by weight solution of ethanol/water at a ratio of 87/13 weight/weight. The solution of the third coating material was applied to 500 grams of the APP45 particles at a rate of about 5.3 to 5.5 grams/minute. The atomizing air pressure for the spray nozzle was about 14–20 PSIG. The fluidizing inlet air temperature varied automatically between 128° F. and 146° F. with a corresponding air discharge temperature of between 94° F.

and 103° F. A sample was taken and sieved and was designated APP46, which comprised 20% by weight zein (F 4000LE) applied as a first coat followed by 16% by weight Eudragit ® as a second coat followed by 23% by weight zein (F 4000LE) as a third coat, with the particles having sizes of less than 297 microns.

The particles produced in this example were subjected to dissolution testing as described in Example 1. Selected particle samples were subjected to sequential dissolution testing as described in Example 2. The results of the dissolution tests are set forth in Table 5.

TABLE 5

Dissolution Of Coated Acetaminophen In Simulated Gastric (pH 1.2) And Intestinal Fluids (pH 6.8)

| Sample | % Drug | Cumulative % Release of APAP | | | | | | 1st coat | 3rd coat |
|---|---|---|---|---|---|---|---|---|---|
| | | In SGF, pH 1.2 | | | In SIF, pH 6.8 | | | | |
| | | 0.5 hr | 1 hr | 2 hr | 1 hr | 3 hr | 6 hr | | |
| APP21 | 100. | 97 | 97 | 98 | 98 | 101 | 102 | — | — |
| APP40 | 80.2 | 82 | 94 | 99 | 70 | 98 | 103 | 23%R | — |
| APP41 | 62.8 | 17 | 22 | 29 | 87 | 103 | 103 | 23%R | — |
| APP42 | 50.4 | 14 | 19 | — | 44 | 63 | 71* | 23%R | 23%R |
| APP44 | 82.0 | 72 | 91 | 98 | 72 | 98 | 101 | 20%LE | — |
| APP45 | 66.7 | 15 | 17 | 22 | 88 | 101 | 101 | 20%LE | — |
| APP46 | 53.7 | 17 | 22 | — | 49 | 69 | 74* | 20%LE | 23%LE |

*sequential dissolution procedure

It may be concluded that at these levels of zein coatings the use of R and LE zein does not significantly effect dissolution results. However, at higher levels of zein, (see samples APP27 and APP32 from Example 3) but in a sequential dissolution for APP27 and APP32 there is a difference because the zein having a lower ash content (LE) slowed the dissolution rate. The ash content of zein and the amount coating can be used varied achieve the desired dosage protocol for any particular active substance.

EXAMPLE 6

In this example, single coated particles were prepared comprising a core material of acetaminophen, coated with zein from different manufacturers: zein from Freeman Industries (F 4000LE) comprising at least 90% protein; zein from Corn Products (lot 1952) comprising at least 90% protein; and zein from Nutrilite (lot 011-09) comprising about 87% protein. Both Corn Products of Pekin, Ill., U.S.A., and Nutrilite of Buena Park, Calif. U.S.A., no longer manufacture zein. Granular acetaminophen was used with a particle size range of about 125-250 microns.

A first batch of particles was prepared using zein from Freeman Industries (F 4000LE). A solution of a coating material was prepared comprising zein (F 4000LE, Freeman Industries) and MCT oil at 7.6% by weight of the zein; prepared as a 20% by weight solution of ethanol/water at a ratio of 87/13 weight/weight. The solution was applied to 800 grams of acetaminophen cores at a rate between 5.0-5.8 grams/minute. The atomizing air pressure for the spray nozzle was about 18 PSIG. The fluidizing inlet air temperature varied automatically between 128° F. and 156° F. with a corresponding air discharge temperature of between 85° F. and 115° F. At various times during the coating procedure samples were taken and were designated: APP48, which comprised coating of 23% by weight zein (F 4000LE); APP49, which comprised a coating of 31% by weight zein (F 4000LE); and APP50, which comprised a coating of 46% by weight zein (F 4000LE).

A second batch of particles was prepared using zein from Corn Products. A solution of a coating material was prepared comprising a 20.0% by weight solution of ethanol/water at a ratio of 87/13 weight/weight, and applied to 1200 grams of acetaminophen. The solution was applied to the acetaminophen cores at a rate of about 6.1 grams/minute. The atomizing air pressure for the spray nozzle was about 18 PSIG. The fluidizing inlet air temperature varied automatically between 122° F. and 132° F. with a corresponding air discharge temperature of between 79° F. and 94° F. Samples were taken and were designated: APP54, which comprised a coating of 22% by weight zein (Corn Products); APP55, which comprised a coating of 30% by weight zein (Corn Products); and APP56, which comprised a coating of 43% by weight zein (Corn Products).

A third batch of particles was prepared using zein from Nutrilite (lot 011-09). A solution of a coating was prepared comprising a 20.0% by weight solution of ethanol/water at a ratio of 87/13 weight/weight. The solution was applied to 1200 grams of acetaminophen cores at a rate of about 6.1-6.2 grams/minute. The atomizing air pressure for the spray nozzle was about 18 PSIG. The fluidizing inlet air temperature varied automatically between 128° F. and 137° F. with a corresponding air discharge temperature of between 85° F. and 95° F. Samples were taken and were designated: APP57, which comprised a coating of 24% by weight zein (Nutrilite); APP58, which comprised a coating of 34% by weight zein (Nutrilite); and APP59, which comprised a coating of 53% by weight zein (Nutrilite).

The particles manufactured in this example were subjected to dissolution testing as described in Example 1. The results of the dissolution tests are set forth in Table 6.

TABLE 6

Dissolution Of Coated Acetaminophen In Simulated Intestinal Fluid (pH 6.8)

| Sample | % Drug | 1 hr | 3 hr | 6 hr |
|---|---|---|---|---|
| APP21 | 100. | 98 | 101 | 102 |
| APP48 | 80.1 | 70 | 98 | 102 |
| APP49 | 74.9 | 47 | 82 | 94 |
| APP50 | 66.7 | 57 | 84 | 100 |
| APP54 | 81.0 | 63 | 99 | 103 |
| APP55 | 75.5 | 57 | 81 | 90 |
| APP56 | 68.5 | 51 | 79 | 90 |
| APP57 | 79.8 | 90 | 101 | 104 |
| APP58 | 73.5 | 85 | 98 | 101 |
| APP59 | 63.8 | 79 | 95 | 100 |

Depending upon the source of zein, which may be extracted by different processes, all zein exhibits varying amounts of effect on the rate of sustained release. The thickness and type of coating may be varied to achieve the desired dosage protocol for a particular active substance.

EXAMPLE 7

The present invention has special utility as a delivery system for β-lactam antibiotics, such as amoxicillin, which should be protected from the acidic environment of the stomach. As utilized hereinafter the term "β-lactam antibiotics" shall mean compounds having a beta-lactam ring as a central structure, i.e., the structure

which thereafter may be substituted at various positions on the ring and/or fused with other ring systems which may themselves be substituted or unsubstituted. Some examples of well-known β-lactam antibiotics include penicillins, cephalosporins, monocyclic β-lactams, e.g. azthreonam, thienamycin and its derivatives, and the clavulanic acid derivatives as well as the pharmaceutically acceptable salts of the above-mentioned compounds.

In this example, dual coated particles were prepared comprising a core material of amoxicillin trihydrate from Interchem Corporation, Paramus, N.J., U.S.A., granulated with zein (F 4000, from Freeman Industries) using a Glatt GPCG 3 and top spray. A solution of a granulating material was prepared comprising zein, MCT oil and amoxicillin trihydrate, with MCT oil equaling 7.6% of the zein, and amoxicillin equaling 80% of the zein, as a 27.1% by weight solution of ethanol/water at a 80/20 weight/weight ratio. The granulating material was then applied to 750.0 grams of amoxicillin trihydrate particles at a rate of about 40.0 grams/minute. The fluidizing inlet air temperature varied automatically between 140° F. and 142° F. with a corresponding product temperature of between 77° F. and 119° F. The particles were sieved to be in a size range of about 100-200 microns. A sample was taken and designated AMX2, amoxicillin granulated with 60% by weight zein.

The particles of sample AMX2 were then coated with zein (F 4000) and then further coated to form a dual coated product of the present invention. A solution of a first coating material was prepared comprising zein (F 4000, Freeman Industries) plus MCT oil equaling 7.6% of the zein, as a 11.4% by weight solution of ethanol/water at a 80/20 weight/weight ratio. The solution of the first coating material was then applied to 750.0 grams of the AMX2 cores at a rate that varied from about 5.5 to 8.4 grams/minute using a fluidized bed coating procedure in a Glatt GPCG 3 with a 7 inch Wurster column insert, and bottom spray. The fluidizing inlet air temperature varied automatically between 113° F. and 115° F. with a corresponding particle temperature of between 70° F. and 95° F. Samples were taken and were designated: AMX3, which comprised AMX2 as the core with a single coat of 47% by weight Zein; and AMX4, which comprised AMX2 as the core with a single coat of 51% by weight zein.

The AMX4 particles were then subjected to a second fluidized bed coating procedure. A solution of a second coating material was prepared comprising a mixture of Eudragit® L 100 and Eudragit® S100, in a 3/1 weight/weight ratio, plus triethyl citrate equaling 15% by weight of the total Eudragit®, plus talc (Alpha-fil 500USP from Cyprus Industrial Minerals Company) equaling 30% by weight of the total Eudragit®, as a 12.0% by weight solution of ethanol/acetone at a 88.7/11.3 weight/weight ratio. The solution of the second coating material was then applied to 750 grams of the AMX4 particles at a rate of about 11.6-11.8 grams/minute to form dually coated particles. The fluidizing inlet air temperature automatically varied between 115° F. and 118° F. with a corresponding air outlet temperature between 104° F. and 110° F. Samples were designated: AMX5, which comprised AMX2 as the core, with 51% by weight zein applied as a first coating and 39% by weight Eudragit® as a second coating; and AMX6, which comprised AMX2 as the core, with 51% by weight zein applied as a first coating and 45% by weight Eudragit® as a second coating.

The particles manufactured in this example were subjected to dissolution testing as described in Example 1. Selected particle samples were subjected to sequential dissolution testing as described in Example 2.

A USP HPLC method (USP XXII—NF XVII, supplement 1, pp. 2088-2089, 1989) was adapted for the determination of amoxicillin in both zein-coated powders and dissolution samples from various media. The column was C-18. The mobile phase was a pH 5.0 potassium phosphate buffer containing 4% acetonitrile, at a flow rate of 1.5 mL/min. The detector was UV at 230 nm. A pure amoxicillin trihydrate (AMX1), which was calibrated with an USP reference standard, was used as the working standard. For dissolution sample analysis, the standard was dissolved in the mobile phase. For zein-coated drug analysis, both the sample and the standard were dissolved by mixing with 5 mL methanol for 2-5 minutes and then diluting with the mobile phase to the desired level.

The results of the dissolution tests are set forth in Table 7.

TABLE 7

Dissolution Of Coated Amoxicillin In Simulated Gastric (pH 1.2) And Intestinal Fluids (pH 6.8)

| Sample | % Drug | Cumulative % Release of Amoxicillin | | | | | |
|---|---|---|---|---|---|---|---|
| | | In SGF, pH 1.2 | | | In SIF, pH 6.8 | | |
| | | 0.5 hr | 1 hr | 2 hr | 1 hr | 3 hr | 6 hr |
| AMX2 | 60.7 | — | — | — | 86 | 85 | 89 |
| AMX3 | 40.2 | — | — | — | 36 | 66 | 79 |
| | | | | | 42 | 60 | 66** |
| AMX4 | 39.1 | — | — | — | 50 | 66 | 77 |
| | | 46 | 43 | — | 80 | 79 | 79* |
| | | | | | 56 | 62 | 63** |
| AMX5 | 25.1 | 18 | 18 | 21 | 46 | 61 | 71 |
| | | 20 | 21 | — | 49 | 60 | 66* |
| AMX6 | 23.6 | 12 | 20 | 25 | 37 | 62 | 75 |
| | | 18 | 27 | — | 69 | 75 | 78* |
| AMX23 | 100.0 | 53 | 45 | 36 | 83 | 91 | 93*** |

*sequential dissolution procedure
**dissolution performed in pH 8.4 buffer
***uncoated particles The dissolution results for the particles made in this example showed that sustained release in simulated intestinal fluid is not achieved merely by granulating an active substance with zein, even at zein levels as high as 65% of the total weight (see AMX2 in Table 7). However, when zein was used as a coating material on this same granulated core, then sustained release in simulated intestinal fluid was achieved.

EXAMPLE 8

In this example, dual coated particles were prepared comprising a core material of amoxicillin trihydrate rotor granulated with zein (F 4000, from Freeman Industries) using a Glatt GPCG 5 with rotor insert. A solution of a granulating material was prepared comprising zein plus MCT oil, with MCT oil equaling 7.6% of the zein, was prepared as a 6.0% by weight solution of ethanol/water at a 80/20 weight/weight ratio. With the rotor turning at 500 RPM, the solution containing 250 grams of zein, was applied to 2.5 kilograms of micronized amoxicillin trihydrate particles, at a rate that varied from about 50.0-65.0 grams/minute. The atomizing air pressure for the spray nozzle varied from 26 to 32 PSIG. The fluidizing inlet air temperature varied automatically while spraying between 86° F. and 95° F. and a corresponding product temperature while spraying between 61° F. and 68° F. Following completion of spraying of the zein solution, 700 grams of distilled water/ethanol at a 57/43 weight/weight ratio, was sprayed on the batch at a rate of about 85.0 grams/minute.

The atomizing air pressure for the spray nozzle was about 26 PSIG. After completion of the water/ethanol spraying, drying air was increased to between 122° F. and 167° F. with a corresponding product temperature while drying between 79° F. and 90° F. The granules were sieved to sizes of: (a) less than 180 microns; (b) greater than 250 microns; and (c) between 180-250 microns.

A solution consisting of the amoxicillin granules greater than 250 microns was prepared as a 11.7% by weight slurry of distilled water/ethanol at a 83/17 weight/weight ratio, respectively. Using a Glatt GPCG 5 with rotor insert, the slurry was applied to 1.703 kilograms of the sieved amoxicillin granules less than 180 microns. With the rotor turning at 500 RPM, the amoxicillin slurry was applied at a rate that varied from about 50.0-62.0 gram/minute. Atomizing air pressure for the spray nozzle varied from 26 to 32 PSIG. A total of 240 grams of ethanol/distilled water at a 80/20 weight/weight ratio was again applied prior to drying at a rate of about 62.0 grams/minute. Atomizing air pressure for the spray nozzle was about 29 PSIG. Drying was terminated when product temperature reached 90° to 93° F. The fluidizing inlet air temperature while spraying was about 86° F., while drying between 104° F. and 167° F. with a corresponding granule temperature while spraying between 64° F. and 68° F., and while drying between 79° F. and 90° F. The granules were sieved to sizes of: (a) less than 125 microns; (b) greater than 250 microns; and (c) between 125-250 microns. The 180-250 micron size granules from both the first and second charges were intimately mixed and sampled. This sample is designated AMX31, amoxicillin rotor granules with 11% by weight zein.

The core particles of sample AMX31 were then coated with zein (F 4000) and then further coated to form a dual coated product of the present invention. A solution of a first coating material was prepared comprising zein (F 4000, Freeman Industries) plus MCT oil equaling 7.6% of the zein, as a 11.4% by weight solution of ethanol/water at a 80/20 weight/weight ratio. The particles were coated by fluidized bed coating procedure in a Glatt GPCG 1 with a 6 inch Wurster column insert, and bottom spray. The solution of the first coating material was applied to 529.0 grams of the AMX31 amoxicillin cores at a rate of about 12.0 grams/minute. Atomizing air pressure for the spray nozzle was about 41 PSIG. The fluidizing inlet air temperature varied automatically between 118° F. and 127° F. with a corresponding product temperature of between 82° F. and 98° F. The particles were then subjected to a second fluidized bed coating procedure. A solution of a second coating material was prepared comprising a mixture of Eudragit ® L 100 and Eudragit ® S100, in a 3/1 weight/weight ratio, plus triethyl citrate equaling 15% by weight of the total Eudragit ®, plus talc (Alpha-fil 500USP from Cyprus Industrial Minerals Company) equaling 30% by weight of the total Eudragit ®, as a 12.0% by weight solution of ethanol/acetone at a 88.7/11.3 weight/weight ratio. The solution of the second coating material was applied to 620 grams of the single coated particles to form dually coated particles at a rate of about 12.0 grams/minute. The atomizing air pressure for the spray nozzle was about 44 PSIG. The fluidizing inlet air temperature automatically varied between 118° F. and 120° F. with a corresponding product temperature between 97° F. and 106° F. Samples were taken and designated as follows: AMX32, which comprised AMX31 as the core, with 45% by weight zein applied as a first coating and 22% by weight Eudragit ® as a second coating; and AMX33, which comprised AMX31 as the core, with 45% by weight zein applied as a first coating and 52% by weight Eudragit ® as a second coating.

The particles were subjected to dissolution as described in Example 1. The dissolution results are presented in Table 8.

TABLE 8

Dissolution Of Coated Amoxicillin In Simulated Gastric (pH 1.2) And Intestinal Fluids (pH 6.8)

| Sample | % Drug | Cumulative % Release of Amoxicillin | | | | | |
|---|---|---|---|---|---|---|---|
| | | In SGF, pH 1.2 | | | In SIF, pH 6.8 | | |
| | | 0.5 hr | 1 hr | 2 hr | 1 hr | 3 hr | 6 hr |
| AMX23 | 100.0 | 53 | 45 | 36 | 83 | 91 | 93** |
| AMX31 | 89.5 | 40 | 33 | 25 | 91 | 88 | 86* |
| AMX32 | 45.5 | 3 | 4 | 9 | 24 | 53 | 77 |
| AMX33 | 34.5 | 3 | 2 | 3 | 20 | 42 | 66 |

*agglomerated core without coating
**uncoated, unagglomerated core

Figure 8:
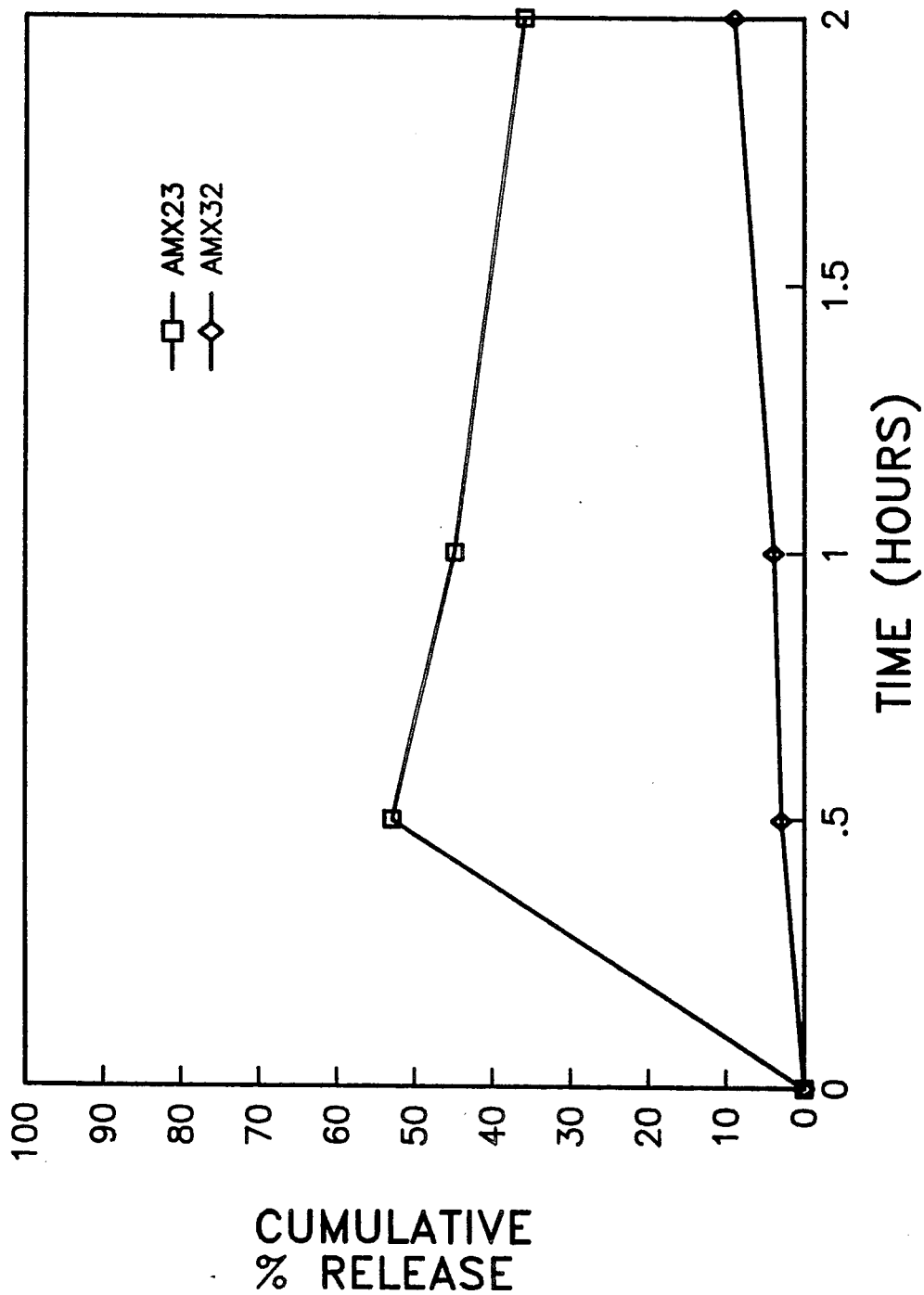
FIG. 8 is a graph showing the dissolution of amoxicillin from the cores of particles having a zein coating over the core and an enteric coating over the zein coating, when the particles were placed in simulated gastric fluid at pH 1.2.
Figure 9:
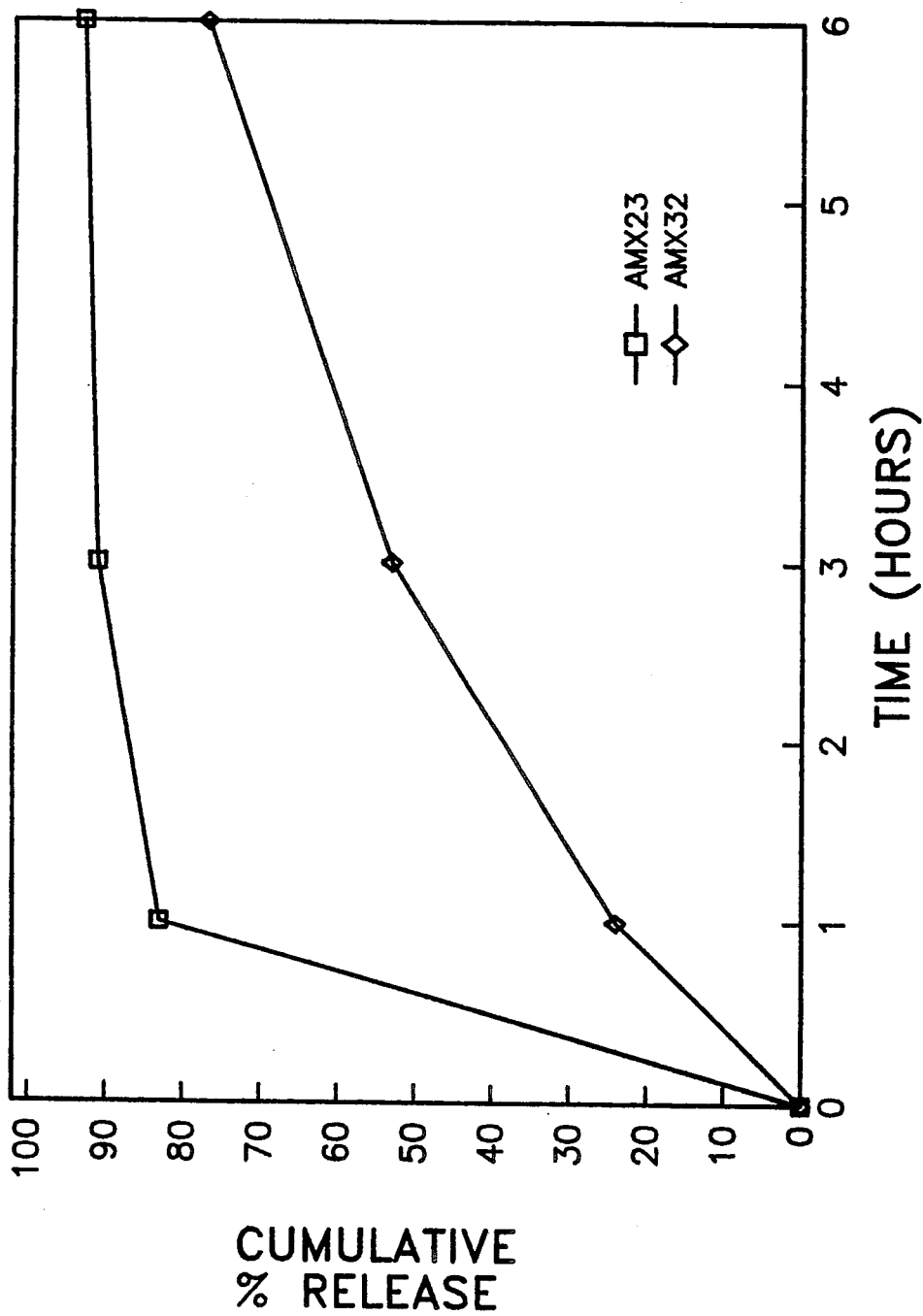
FIG. 9 is a graph showing the dissolution of amoxicillin from the cores of particles having a zein coating over the core and a second enteric coating over the zein coating, when the particles were placed in simulated intestinal fluid at pH 6.8.

The dissolution results for particles from samples AMX23 (uncoated, unagglomerated amoxicillin) and AMX32 (agglomerated amoxicillin core, first coat zein and exterior coat of an Eudragit ® compound) are presented in FIGS. 8 and 9. In simulated gastric fluid (FIG. 8) the uncoated AMX23 had a rapid release, but the release of the active substance from the double coated AMX32 was minimal. This confirms the dissolution results for dual coated APAP cores shown in FIG. 3.

The dissolution results for AMX23 and AMX32 in simulated intestinal fluid are presented in FIG. 9. Once again, as already demonstrated in FIG. 4 for APAP, the active substance was released in sustained manner from the double coated core, but quite rapidly when the active substance was not coated.

EXAMPLE 9

In this example, triple coated particles were prepared comprising a core material of amoxicillin trihydrate rotor granulated with zein (F 4000, from Freeman Industries) using a Glatt GPCG 5 with rotor insert. A solution of a granulating material was prepared comprising zein plus MCT oil, with MCT oil equaling 7.6% of the zein, as a 6.0% by weight solution of ethanol/water at a 80/20 weight/weight ratio. To this granulating solution was added 445 grams of amoxicillin trihydrate. With the rotor turning at 500 RPM, the slurry containing 250 grams of zein and 445 grams of amoxicillin was applied to 2,055 grams of amoxicillin trihydrate micronized particles at a rate that varied from about 52.0–63.0 grams/minute. The atomizing air pressure for the spray nozzle varied from about 24–27 PSIG. Following the zein/amoxicillin slurry, 200 grams of distilled water/ethanol at a 83/17 weight/weight ratio was then applied at a rate of about 63.0 grams/minute. The fluidizing inlet air temperature varied automatically while spraying between 102° F. and 104° F., and during drying about 122° F. with a corresponding granule temperature while spraying between 59° F. and 63° F., and while drying about 91° F. The granules were sieved to less than 180 microns, greater than 250 microns, and between 180–250 microns. A slurry consisting of 386 grams of the amoxicillin granules greater than 250 microns was prepared as a 11.7% by weight slurry of distilled water/ethanol at a 83/17 weight/weight ratio. Using a Glatt GPCG 5 with rotor insert, the slurry was applied to 1,295 grams of the sieved amoxicillin granules having sizes of less than 180 microns. With the rotor turning at 500 RPM, the amoxicillin slurry was applied at a rate of about 52.0 grams/minute. The atomizing air pressure for the spray nozzle was about 24 PSIG. A total of 200 grams of ethanol/distilled water at a 80/20 weight/weight ratio was applied prior to drying at a rate of about 62.0 grams/minute. The atomizing air pressure for the spray nozzle was about 24 PSIG. Drying was terminated when product temperature reached 90° F. The fluidizing inlet air temperature while spraying was about 104° F. and while drying about 122° F. with a corresponding granule temperature while spraying between 64° F. and 68° F., and while drying about 90° F. The granules were sieved to sizes of: (a) less than 180 microns; (b) greater than 250 microns; and (c) between 180–250 microns. A slurry consisting of 100 grams of the amoxicillin granules greater than 250 microns was prepared as a 11.7% by weight slurry of distilled water/ethanol at a 83/17 weight/weight ratio.

Using a Glatt GPCG 5 with rotor insert, the slurry was applied to 1,300 grams of the sieved amoxicillin granules having sizes of less than 180 microns. With the rotor turning at 500 RPM, the amoxicillin slurry was applied at a rate of about 52.) grams/minute. The atomizing air pressure for the spray nozzle was about 24 PSIG. A total of 200 grams of ethanol/distilled water at a 80/20 weight/weight ratio was again applied prior to drying at a rate of about 62.0 grams/minute. The atomizing air pressure for the spray nozzle was about 24 PSIG. Drying was terminated when product temperature reached 90° F. The fluidizing inlet air temperature while spraying was about 104° F., and while drying about 122° F. with a corresponding granule temperature while spraying between 62° F. and 68° F., and while drying about 90° F. The granules were sieved to sizes of: (a) less than 180 microns; (b) greater than 250 microns; and (c) between 180–250 microns.

The 180–250 micron size granules from the first, second, and third charges were intimately mixed and sampled. This sample was designated AMX34-1, amoxicillin rotor granules with 17% by weight zein.

Particles from sample AMX34-1 were then coated with zein (F 4000,), then further coated to form a dual coated product of the present invention, and finally further coated to form a triple coated product of the present invention. The particles were coated by fluidized bed coating procedure in a Glatt GPCG 1 with a 6 inch Wurster column insert, and bottom spray. A solution of a first coating material was prepared comprising zein (F 4000, Freeman Industries) plus MCT oil equaling 7.8% of the zein, as a 11.4% by weight solution of ethanol/water at a 80/20 weight/weight ratio. The solution containing zein was applied to 600 grams of rotor granules represented by sample AMX34-1 at a rate of about 15.0 grams/minute. The atomizing air pressure for the spray nozzle was about 41 PSIG. The fluidizing inlet air temperature varied automatically between 116° F. and 138° F. with a corresponding product temperature of between 72° F. and 99° F. Samples were taken and designated as follows: AMX35B, comprising AMX34-1 as the core, with 17% by weight zein applied as a first coating; and AMX36B, comprising AMX34-1 as the core, with 30% by weight zein applied as the first coating. The particles represented by sample AMX36B were then subjected to a second fluidized bed coating procedure.

A solution of a second coating material was prepared comprising a mixture of Eudragit ® L 100 and Eudragit ® S 100, in a 3/1 weight/weight ratio, plus triethyl citrate equaling 15% by weight of the total Eudragit ®, as a 12.0% by weight solution of ethanol/acetone/water at a 84.2/11.3/4.5 weight/weight/weight ratio. The solution of the second coating material was applied to 700 grams of the single coated AMX36B particles to form dually coated particles at a rate of about 14–16.0 grams/minute. The atomizing air pressure for the spray nozzle was about 44 PSIG. The fluidizing inlet air temperature automatically varied between 118° F. and 142° F. with a corresponding product temperature between 88° F. and 102° F. Samples were taken and designated as follows: AMX37B, which comprised AMX34-1 as the core, with 30% by weight zein applied as a first coating and 8% by weight Eudragit ® as a second coating; and AMX38B, which comprised AMX34-1 as the core, with 30% by weight zein applied as a first coating and 16% by weight Eudragit ® as a second coating. A solution of a third coating material was prepared comprising zein (F 4000LE, Freeman Industries) plus MCT oil equaling 7.6% of the zein, as a 11.4% by weight solution of ethanol/water at a 80/20 weight/weight ratio. The solution containing zein was applied to 655 grams of the dual coated particles of AMX38B at a rate between about 14.0–16.0 grams/minute. The atomizing air pressure for the spray nozzle was about 41 PSIG. The fluidizing inlet air temperature varied automatically between 117° F. and 140° F. with a corresponding product temperature of between 79° F. and 106° F.

Samples were taken and designated as follows: AMX39, comprising AMX34-1 as the core, with 30% by weight zein (F 4000) applied as a first coating, 16% by weight Eudragit ® as a second coating, and 74% zein (F 4000LE) as a third coating; and AMX40, comprising AMX34-1 as the core, with 30% by weight zein (F 4000) applied as a first coating, 16% by weight Eudragit ® as a second coating, and 76% zein (F 4000LE) as a third coating.

A second batch of triple coated particles was the produced using the following procedure. A second batch of amoxicillin rotor particles were produced using the same procedure as used in making the sample designated AMX34-1, but with a different ratio of zein to amoxicillin. This sample was designated AMX34, amoxicillin rotor granules with 30% by weight zein. Particles from sample AMX34 were then coated with zein (F 4000), then further coated to form a dual coated product of the present invention, and finally further coated to form a triple coated product of the present invention. The particles were coated by fluidized bed coating procedure in a Glatt GPCG 1 with a 6 inch Wurster column insert, and bottom spray. A solution of a first coating material was prepared comprising zein (F 4000, Freeman Industries) plus MCT oil equaling 7.6% of the zein, as a 11.4% by weight solution of ethanol/water at a 80/20 weight/weight ratio. The solution containing zein was applied to 750 grams of rotor granules represented by sample AMX34 at a rate of about 15.0 grams/minute. The atomizing air pressure for the spray nozzle was about 41 PSIG. The fluidizing inlet air temperature varied automatically between 116° F. and 138° F. with a corresponding product temperature of between 63° F. and 95° F. The particles were then subjected to a second fluidized bed coating procedure. A solution of a second coating material was prepared comprising a mixture of Eudragit ® L 100 and Eudragit ® S100, in a 3/1 weight/weight ratio, plus talc (Alpha-fil 500USP from Cyprus Industrial Minerals Company) equaling 30% by weight of the total Eudragit ®, plus triethyl citrate equaling 15% by weight of the total Eudragit ®, as a 12.0% by weight solution of ethanol/acetone/water at a 84.2/11.3/4.5 weight/weight/weight ratio. The solution of the second coating material was applied to 750 grams of the single coated particles to form dually coated particles at a rate of about 10.0–16.0 grams/minute. The atomizing air pressure for the spray nozzle was about 44 PSIG. The fluidizing inlet air temperature automatically varied between 120° F. and 140° F. with a corresponding product temperature between 84° F. and 99° F. Samples were taken and designated as follows: AMX42, which comprised AMX34 as the core, with 10% by weight zein applied as a first coating and 14% by weight Eudragit ® as a second coating; and AMX43, which comprised AMX34 as the core, with 10% by weight zein applied as a first coating and 23% by weight Eudragit ® as a second coating. A solution of a third coating material was prepared comprising zein (F 4000LE, Freeman Industries) plus MCT oil equaling 7.6% of the zein, as a 11.4% by weight solution of ethanol/water at a 80/20 weight/weight ratio. The solution containing zein was applied to 560 grams of the dual coated particles of AMX43 at a rate between about 13–21 grams/minute. The atomizing air pressure for the spray nozzle was about 41 PSIG. The fluidizing inlet air temperature varied automatically between 118° F. and 129° F. with a corresponding product temperature of between 77° F. and 100° F. Samples were taken and designated as follows: AMX44, comprising AMX34 as the core, with 10% by weight zein (F4000) applied as a first coating, 23% by weight Eudragit ® as a second coating, and 75% zein (F 4000LE) as a third coating; and AMX45, comprising AMX34 as the core, with 10% by weight zein (F 4000) applied as a first coating, 23% by weight Eudragit ® as a second coating, and 95% zein (F 4000LE) as a third coating.

A third batch of triple coated particles was then produced using the following procedure. The same batch of amoxicillin rotor particles designated by sample AMX34, amoxicillin rotor granules with 30% by weight zein, was used to produce this triple coated product. Particles from sample AMX34 were coated with zein (F 4000), then further coated to form a dual coated product of the present invention, and finally further coated to form a triple coated product of the present invention. The particles were coated by fluidized bed coating procedure in a Glatt GPCG 1 with a 6 inch Wurster column insert, and bottom spray. A solution of a first coating material was prepared comprising zein (F 4000, Freeman Industries) plus MCT oil equaling 7.6% of the zein, as a 11.4% by weight solution of ethanol/water at a 80/20 weight/weight ratio. The solution containing zein was applied to 325 grams of rotor granules represented by sample AMX34 at a rate of about 15.0 grams/minute. The atomizing air pressure for the spray nozzle was about 41 PSIG. The fluidizing inlet air temperature varied automatically between 120° F. and 140° F. with a corresponding product temperature of between 63° F. and 93° F. A sample was taken and designated AMX46, which comprised AMX34 as the core, with 80% by weight zein applied as a first coating. The particles were then subjected to a second fluidized bed coating procedure. A solution of a second coating material was prepared comprising a mixture of Eudragit ® L 100 and Eudragit ® S 100, in a 3/1 weight/weight ratio, plus talc (Alpha-fil 500USP from Cyprus Industrial Minerals Company) equaling 30% by weight of the total Eudragit ®, plus triethyl citrate equaling 15% by weight of the total Eudragit ®, as a 12.0% by weight solution of ethanol/acetone/water at a 84.2/11.3/4.5 weight/weight/weight ratio. The solution of the second coating material was applied to 275 grams of the single coated particles of AMX46 to form dually coated particles at a rate of about 10.0 grams/minute. The atomizing air pressure for the spray nozzle was about 44 PSIG. The fluidizing inlet air temperature automatically varied between 120° F. and 140° F. with a corresponding product temperature between 90° F. and 108° F. Samples were taken and designated as follows: AMX47, which comprised AMX34 as the core, with 80% by weight zein applied as a first coating and 12% by weight Eudragit ® as a second coating; and AMX48, which comprised AMX34 as the core, with 80% by weight zein applied as a first coating and 20% by weight Eudragit ® as a second coating. A solution of a third coating material was prepared comprising zein (F 4000LE, Freeman Industries) plus MCT oil equaling 7.7% of the zein, as a 11.4% by weight solution of ethanol/water at a 80/20 weight/weight ratio. The solution containing zein was applied to 277 grams of the dual coated particles at a rate of about 14 grams/minute. The atomizing air pressure for the spray nozzle was about 41 PSIG. The fluidizing inlet air temperature varied automatically between 118° F. and 138° F. with a corresponding product temperature of between 77° F. and 100° F. Samples were taken and designated as follows: AMX49, comprising AMX34 as the core, with 80% by weight zein (F 4000) applied as a first coating, 20% by weight Eudragit ® as a second coating, and 70% zein (F 4000LE) as a third coating; and AMX50, comprising AMX34 as the core, with 80% by weight zein (F 4000) applied as a first coating, 20% by weight Eudragit ® as a second coating, and 78% zein (F 4000LE) as a third coating.

The particles produced in this example were subjected to dissolution in the manner set forth in Example 1. Some particles were subjected to sequential dissolution in the manner set forth in Example 2. The results are presented in Table 9.

TABLE 9

Dissolution Of Coated Amoxicillin In Simulated Gastric (pH 1.2) And Intestinal Fluids (pH 6.8)

| | | Cumulative % Release of Amoxicillin | | | | | |
|---|---|---|---|---|---|---|---|
| | | In SGF, pH 1.2 | | | In SIF, pH 6.8 | | |
| Sample | % Drug | 0.5 hr | 1 hr | 2 hr | 1 hr | 3 hr | 6 hr |
| AMX34 | 75.6 | 61 | 48 | 36 | 103 | 108 | 108 |
| AMX35B | 71.4 | 31 | 22 | 5 | 102 | 100 | 93 |
| AMX36B | 64.1 | 27 | 6 | 4 | 76 | 87 | 87 |
| AMX37B | 57.4 | 51 | 46 | 32 | 81 | 82 | 84 |
| AMX38B | 52.3 | 14 | 4 | 4 | 79 | 86 | 86 |
| AMX39 | 29.2 | 21 | 28 | — | 44 | 51 | 51* |
| AMX40 | 28.8 | 16 | 23 | — | 36 | 45 | 45* |
| AMX42 | 56.6 | 47 | 43 | 36 | 104 | 111 | 109 |
| AMX44 | 28.4 | 11 | 15 | — | 29 | 40 | 48* |
| AMX45 | 25.7 | 9 | 15 | — | 36 | 57 | 66* |
| AMX48 | 31.6 | 33 | 40 | — | 55 | 62 | 67* |
| AMX49 | 18.1 | 6 | 10 | — | 16 | 20 | 26* |
| AMX50 | 17.2 | 4 | 7 | — | 12 | 15 | 23* |

*sequential dissolution procedure

Figure 10:
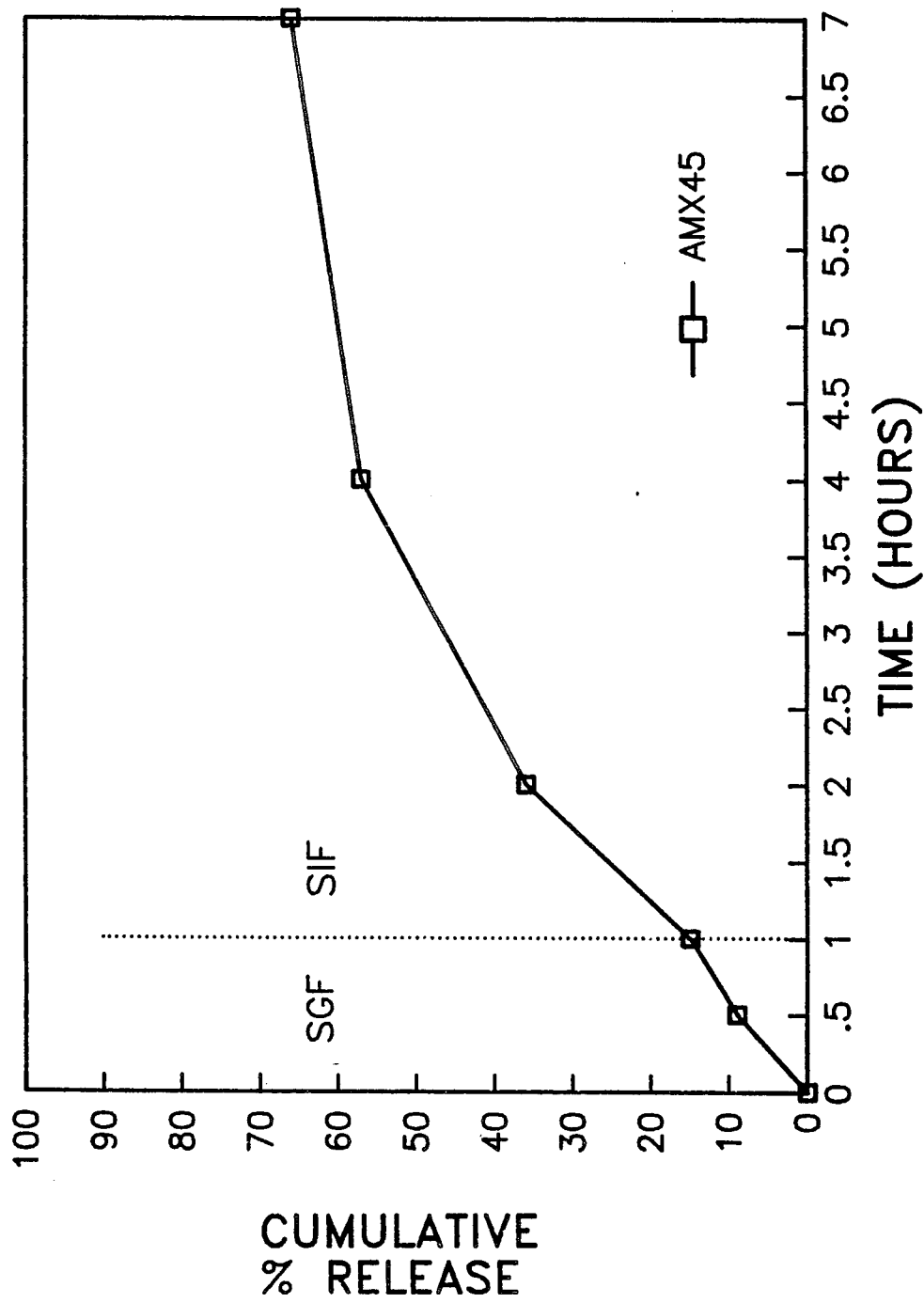
FIG. 10 is a graph showing the dissolution of amoxicillin from the cores of particles having a first zein coating over the core, with a second enteric coating over the first zein coating, followed by a second coating of zein over the enteric coating, when the particles were sequentially placed in simulated gastric fluid at pH 1.2 for one hour, followed by placement in simulated intestinal fluid at pH 6.8 for six hours.

The sequential dissolution results for triple coated particles from sample AMX45 are presented in a graph in FIG. 10. The desired sustained release of the active substance in simulated intestinal fluid (SIF) was achieved, while there was minimal release of the active substance in simulated gastric fluid (SGF). This confirms the sequential dissolution results for triple coated APAP which are presented in FIG. 7.

It was further concluded from the dissolution results presented in Table 9 that both of the zein coating layers in a triple coated particle contribute to the rate of release in simulated intestinal fluid. (Compare the dissolution results for AMX39, 40, 44, 49 and 50.)

EXAMPLE 10

In this example, dual coated particles were prepared comprising a core material of amoxicillin trihydrate rotor granulated with zein (F 4000, from Freeman Industries) using a Glatt GPCG 5 with rotor insert. A solution of a granulating material was prepared comprising zein plus MCT oil, with MCT oil equaling 7.6% of the zein, as a 6.0% by weight solution of ethanol/water at a 80/20 weight/weight ratio. With the rotor turning at 300 RPM, the slurry containing 150 grams of zein was applied to 2,500 grams of micronized amoxicillin trihydrate particles at a rate about 51 grams/minute. The atomizing air pressure for the spray nozzle was about 32 PSIG. Following the spraying of the zein solution, the unit was shut down without drying the batch. The Glatt GPCG 5's filter was discharged into a sheet of plastic sheeting. This 442 grams of filter product was then slurried into 1625 grams of ethanol/distilled water at a 60/40 weight/weight ratio. This slurry was then applied at a rate of about 51.0 grams/minute. Distilled water was then sprayed at about 51 grams/minute until the rotor torque reached 52.0 Newton-Meters. At this point the rotor RPM was increased from 300 to 500 RPM and drying was started. The fluidizing inlet air temperature while spraying the zein solution and the filter particle slurry was about 86° F., and during drying between about 122°-167° F. with a corresponding granule temperature while spraying between 49° F. and 70° F., and while drying about 95° F. The granules were sieved to less than 100 microns, greater than 125 microns, and between 100-125 microns. The 100-125 micron size granules were sampled. This sample is designated AMX62, amoxicillin rotor granules with 7% by weight zein.

Particles from sample AMX62 were then coated with zein (F 4000LE), then further coated to form a dual coated product of the present invention. The particles were coated by a fluidized bed coating procedure in a Glatt GPCG 1 with a 6 inch Wurster column insert, and bottom spray. A solution of a first coating material was prepared comprising Zein (F 4000LE), Freeman Industries) plus MCT oil equaling 7.6% of the zein, as a 11.4% by weight solution of ethanol/water at a 80/20 weight/weight ratio. The solution containing zein was applied to 500 grams of rotor granules represented by sample AMX62 at a rate of about 9-10 grams/minute. The atomizing air pressure for the spray nozzle was about 47 PSIG. The fluidizing inlet air temperature varied automatically between 125° F. and 127° F. with a corresponding product temperature of between 90° F. and 100° F. A sample was taken and designated AMX63, which comprised AMX62 as the core, with 21% by weight zein (F 4000LE) applied as a first coating. The particles represented by sample AMX63 were then subjected to a second fluidized bed coating procedure. A solution of a second coating material was prepared comprising a mixture of Eudragit ® L 100 and Eudragit ® S 100, in a 3/1 weight/weight ratio, plus talc (Alpha-fil 500USP from Cyprus Industrial Minerals Company) equaling 30% by weight of the total Eudragit ®, plus triethyl citrate equaling 15% by weight of the total Eudragit ®, as a 12.0% by weight solution of ethanol/acetone/water at a 84.2/11.3/4.5 weight/weight/weight ratio. The solution of the second coating material was applied to 469 grams of the single coated particles to form dually coated particles at a rate of about 8-10.0 grams/minute. The atomizing air pressure for the spray nozzle was about 44 PSIG. The fluidizing inlet air temperature automatically controlled to 122° F, with a corresponding product temperature between 93° F. and 97° F. Samples were taken and designated: AMX64, which comprised AMX62 as the core, with 21% by weight zein (F 4000LE) applied as a first coating and 29% by weight Eudragit ® as a second coating; and AMX65, which comprised AMX62 as the core, with 21% by weight zein (F 4000LE) applied as a first coating and 67% by weight Eudragit ® as a second coating.

TABLE 10

Dissolution Of Coated Amoxicillin In Simulated Gastric (pH 1.2) And Intestinal Fluids (pH 6.8)

| | | Cumulative % Release of Amoxicillin | | | | | |
|---|---|---|---|---|---|---|---|
| | | In SGF, pH 1.2 | | | In SIF, pH 6.8 | | |
| Sample | % Drug | 0.5 hr | 1 hr | 2 hr | 1 hr | 3 hr | 6 hr |
| AMX36 | 76.4 | 54 | 46 | — | 47 | 48 | 50 |
| AMX64 | 53.6 | 3 | 6 | — | 14 | 22 | 35 |
| AMX65 | 38.8 | 2 | 2 | — | 6 | 14 | 29 |
| | | 3 | 3 | — | 8 | 19 | 38 |

Only zein having a very low ash content by weight of less than 0.1% (zein F 4000LE from Freeman Industries) was used in the particles made in this example. Even when used sparingly, the lower ash content zein had a positive effect in retarding the release of the active substance from the core. Lower ash content zein may be used when the size of particles due to coating thicknesses becomes a critical factor in a particular application of the invention.

EXAMPLE 11

Amoxicillin trihydrate was coated with different combinations and concentrations of zein (regular and LE grades) and Eudragit ® (L100 plus S100 in a ratio of 3:1 weight/weight) as shown in Table 11. The particles designated AMX1 are uncoated particles of amoxicillin. A description of the manufacture of the AMX65 particles is set forth in Example 10; for the AMX44 and AMX49 particles in Example 9.

The purpose of this example is to demonstrate that particles in accordance with the invention may be disposed in a liquid medium to provide an alternative system for delivery of an active substance for release in the intestinal tract. As used herein and in the claims, a "liquid medium" is understood to be an oil based liquid, aqueous based liquid, or a liquid that has a base which is a combination of water and oil. As used herein and in the claims, a "liquid" is understood to mean a state of matter in which the molecules are relatively free to change their positions with respect to each other but are restricted by cohesive forces to maintain a relatively fixed volume.

TABLE 11

Composition of Microencapsulated Amoxicillin Products Tested in Suspension Stability Study

| Sample ID Code | Percent Amoxicillin | Coating Composition and Concentrations | | |
|---|---|---|---|---|
| | | First Coat | Second Coat Eudragit ® | Third Coat |
| | | Zein LE | | |
| AMX 1 | 100 | — | — | — |
| AMX 65 | 38.8 | 21 | 67 | |
| | | Zein Regular | | Zein LE |
| AMX 44 | 28.4 | 10 | 23 | 75 |
| AMX 49 | 18.1 | 80 | 20 | 70 |

Samples of particles having each of the structure from Table 11 were suspended at a concentration of 250 mg amoxicillin per 5 ml in sucrose-based syrups adjusted to different pH's, the formulations of these syrups are set forth in Table 12, were stored at 30° C. and shaken daily. Samples were removed for testing at 1 hours, 1 day, 7 days and 14 days. Encapsulated drug and undissolved particulate matter were removed from the suspensions by filtration through a 35 micron filter. The clarified syrups were diluted with mobile phase of pH 5.0 potassium phosphate buffer containing 4% acetonitrile and filtered again through a 0.45 micron filter prior to analysis by high pressure liquid chromatography (HPLC). The method of quantitating the amount of amoxicillin released in the syrup solutions was adapted from the USP method for amoxicillin described on pages 2088-2089 of Supplement 1 in USP XXII-NF XVII.

TABLE 12

Composition of Syrups for Microencapsulated Amoxicillin Suspension Stability Study

| Ingredient | Syrup A pH 5.0 ± 0.1 | Syrup B pH 6.5 ± 0.1 | Syrup C pH 8.5 ± 0.1 |
|---|---|---|---|
| Sucrose | 89.21 gm | 89.21 gm | 89.21 gm |
| Potassium Sorbate | 0.595 gm | 0.595 gm | 0.595 gm |
| Xanthan Gum | 0.222 gm | 0.222 gm | 0.222 gm |
| Citric Acid | 1.033 gm | 0.101 gm | — |
| Sodium Citrate | 3.332 gm | 6.319 gm | — |
| Sodium Bicarbonate | — | — | 1.478 gm |
| Sodium Carbonate | — | — | 0.1 gm |
| Water | 100 mL | 100 mL | 100 mL |

Table 13 shows that very little amoxicillin was released from samples AMCX 44, 49 and 65 during the test period. Each of these samples had at least one coating layer of zein encapsulating the core. Sample AMX1 was uncoated amoxicillin. This was true regardless of the pH of the syrup. It is believed that at least some of the "release" at one hour was actually fines and uncoated particles from the coating process. The syrup formulation was designed to minimize the solubility of amoxicillin so one would not expect a high rate of release (see results of the uncoated amoxicillin, AMX 1). The slow rate of release in the syrup, however, is thought to be largely due to the 67 percent overcoat of Eudragit ® in AMX 65, and the 75 and 70 percent zein LE outer coats in AMX 44 and 49, respectively.

TABLE 13

Effect of Coating Composition and Syrup pH on the Release of Amoxicillin Microencapsulated with Two Kinds of Zein and Eudragit ®

| Sample Code | Percent Amoxicillin | Percent Amoxicillin Released in Syrup (Storage Time) | | | |
|---|---|---|---|---|---|
| | | 1 Hr | 1 Day | 7 Days | 14 Days |
| | | Syrup at pH 5.0 | | | |
| AMX 1 | 100 | 7.4 | 9.3 | 11.3 | 9.0 |
| AMX 65 | 38.8 | 0.8 | 1.1 | 1.2 | 0.5 |
| AMX 44 | 28.4 | 1.5 | 1.7 | 2.5 | 1.7 |
| AMX 49 | 18.1 | 0.3 | 0.3 | 1.2 | 1.1 |
| | | Syrup at pH 6.5 | | | |
| AMX 1 | 100 | 8.6 | 9.6 | 14.6 | 10.9 |
| AMX 65 | 38.8 | 1.8 | 1.6 | 2.4 | 1.4 |
| AMX 44 | 28.4 | 1.9 | 2.0 | 2.9 | 1.8 |
| AMX 49 | 18.1 | 0.2 | 1.0 | 2.1 | 1.3 |
| | | Syrup at pH 8.5 | | | |
| AMX 1 | 100 | 19.5 | 2.8 | 9.6 | 5.7 |
| AMX 65 | 38.8 | 3.0 | 0.3 | 1.5 | 2.3 |
| AMX 44 | 28.4 | 2.0 | 0.1 | 0.7 | 0.5 |
| AMX 49 | 18.1 | 0.3 | 0.1 | 1.3 | 0.7 |

The concept that stability in an aqueous suspension is primarily controlled by the exterior coating layer is supported by studies performed on acetaminophen (APAP). Acetaminophen was coated with various combinations of zein and Eudragit ®. Table 14 shows the formulations of the syrups in which the various particles were suspended. The composition of these syrups was similar to those used for the amoxicillin suspensions (compare Tables 12 and 14). A description of the manufacture of the APP27 particles is set forth above in Example 3; for APP32 particles in Example 3; for APP42 particles in Example 5; and for APP46 particles in Example 5. The particles identified in the tables as as "APAP" are uncoated acetaminophen. APP27 and 32 were suspended at 250 mg per 5 ml in a syrup at pH 8.1 and APP42 and 46 were each suspended at the same concentration in syrups at both pH 5.0 and 8.1 respectively.

For analysis of samples in sucrose-based syrups, the samples were diluted 50-400 folds with water and then filtered through a 0.45 micron filter for HPLC analysis. The dilution was necessary for proper UW detection and to minimize the effect of matrix on column performance. The methanol content of the aqueous mobile phase was adjusted between 2 and 15%, pending the performance of the C-18 column used.

Tables 15 and 16 show that the particles were not coated well enough to prevent leakage of the drug into the syrup. They do show that the highest concentrations of regular or LE grade zein in the outer coat have the lowest amount of acetaminophen released. The underlying coats may contribute to the relative stability of APP 27 and 32, but it appears that stability must be controlled predominately by the concentration of the outer coat when one compares the release of drug and the concentration of the first and second coating layers of APP 42 and APP 46 with AMX 44 (Tables 16 and 13).

TABLE 14

Composition of Syrups per 150 mL for Microencapsulated Acetaminophen Suspension Stability Studies

| Ingredient | Syrup A pH 5.0 | Syrup B pH 8.1 |
|---|---|---|
| Sucrose | 96.727 gm | 96.727 gm |
| Potassium Sorbate | 0.645 gm | 0.645 gm |
| Xanthan Gum | 0.242 gm | 0.242 gm |
| Silica Gel | 0.322 gm | 0.322 gm |
| Sodium Bicarbonate | 1.612 gm | 1.612 gm |
| Flavoring | 0.451 gm | 0.451 gm |
| Deionized Water | 97.8 mL | 100.0 mL |
| Concentrated HCl | 2.2 mL | — |
| Approximate Volume | 150.0 mL | 150.0 mL |

TABLE 15

Effect of Different Coating Concentrations of Zein and Eudragit ® on the Stability of Microencapsulated APAP in a Syrup at pH 8.1

| Sample Code | Percent APAP | Percent APAP Released in Syrup (Storage Time) | | | | | |
|---|---|---|---|---|---|---|---|
| | | 1 Hr. | 5 Hr. | 1 Day | 7 Days | 14 Days | 28 Days |
| APP 27 | 32.9 | 1.4 | 1.8 | 2.7 | 5.4 | 5.6 | 8.1 |
| APP 32 | 36.5 | 1.6 | 2.7 | 4.8 | 8.1 | 10.0 | 12.0 |
| APAP | 99.6 | 20.0 | ND | ND | ND | ND | 23.0 |
| Syrup | 0 | 0 | ND | ND | ND | ND | 0 |

ND = Not Determined

TABLE 16

Effect of Diffrent Coating Concentrations of Zein and Eudragit ® on the Stability of Microencapsulated APAP in Syrups at pH 5.0 and 8.1

| Sample Code | Percent APAP | pH | Percent APAP Released in Syrup (Storage Time) | | | |
|---|---|---|---|---|---|---|
| | | | 1 Hr | 1 Day | 7 Days | 14 Days |
| APP 42 | 50.4 | 5.0 | 4.0 | 11.3 | 15.0 | 15.0 |
| | | 8.1 | 3.2 | 12.3 | 19.8 | 20.5 |
| APP 46 | 53.7 | 5.0 | 7.2 | 13.4 | 17.5 | 16.2 |
| | | 8.1 | 3.5 | 16.3 | 16.5 | 28.0 |
| APAP | 99.6 | 5.0 | 20.2 | 31.9 | 26.5 | 24.9 |
| | | 8.1 | 7.7 | 27.5 | 29.8 | 28.0 |

This example shows that a suspension containing particles having an active substance in a core coated with at least one layer of a prolamine and one layer of an enteric substance has been reduced to practice, with minimal leakage of the active substance into the suspension medium.

While certain representative embodiments and details have been described for the purpose of illustrating the invention, it will be apparent to those skilled in the art that various changes and modifications may be made therein without departing from the spirit or scope of the invention.

What is claimed is:

1. A system for delivery of an active substance for sustained release in the intestinal tract, comprising a particle having a core containing an active substance, said core being encapsulated by at least two layers of coating materials, one of said layers of a coating material consisting essentially of a prolamine and at least one material selected from the group consisting of plasticizers and hydrophobic substances and the other layer a coating material consisting essentially of an enteric compound and at least one material selected from the group consisting of plasticizers and anti-tackiness agents, such that said other layer is generally resistant to disintegration in human gastric juices but will disintegrate in human intestinal fluids.

2. A system for delivery of an active substance for sustained release in the intestinal tract according to claim 1 wherein the core is encapsulated by a first layer of a coating material, consisting essentially of a prolamine and at least one material selected from the group consisting of plasticizers and hydrophobic substances said first layer is encapsulated by an exterior layer of a coating material consisting essentially of an enteric compound and at least one material selected from the group consisting of plasticizers and anti-tackiness agents, such that said exterior layer is generally resistant to disintegration in human gastric juices but will disintegrate in human intestinal fluids.

3. A system for delivery of an active substance for sustained release in the intestinal tract according to claim 1 wherein the core is encapsulated by a first layer of a coating material consisting essentially of an enteric compound and at least one material selected from the group consisting of plasticizers and anti-tackiness agents, such that said first layer is generally resistant to disintegration in human gastric juices but will disintegrate in human intestinal fluids, and said first layer is encapsulated by an exterior layer of a coating material consisting essentially of a prolamine and at least one material selected from the group consisting of plasticizers and hydrophobic substances.

4. A system for delivery of an active substance for sustained release in the intestinal tract according to claim 1 wherein the core is encapsulated by a first layer comprising a coating material consisting essentially of a prolamine and at least one material selected from the group consisting of plasticizers and hydrophobic substances, said first layer is encapsulated by a second layer comprising a coating material consisting essentially of an enteric compound and at least one material selected from the group consisting of plasticizers and anti-tackiness agents, such that said second layer is generally resistant to disintegration in human gastric juices but will disintegrate in human intestinal fluids, and said second layer is encapsulated by an exterior layer comprising a coating material consisting essentially of a prolamine and at least one material selected from the group consisting of plasticizers and hydrophobic substances.

5. A system for delivery of an active substance for sustained release in the intestinal tract according to any one of claims 1 through 4 wherein the prolamine is zein.

6. A system for delivery of an active substance for sustained release in the intestinal tract according to any one of claims 1 through 4 wherein the enteric compound comprises at least one material selected from the group consisting of acids and esters of methacrylic copolymers.

7. A system for delivery of an active substance for sustained release in the intestinal tract according to claim 5 wherein the enteric compound comprises at least one material selected from the group consisting of acids and esters of methacrylic copolymers.

8. A system for delivery of an active substance for sustained release in the intestinal tract according to any one of claims 1 through 4 comprising a plurality of said particles where in the particles have a size of not greater than about 700 microns, and the system further comprises a liquid medium, said particles being disposed within said liquid medium.

9. A system for delivery of an active substance for release in the intestinal tract according to claim 8 wherein the liquid medium is an aqueous medium.

10. A system for delivery of an active substance for release in the intestinal tract according to claim 9 wherein the prolamine is zein and the enteric compound comprises at least one material selected from the group consisting of acids and esters of methacrylic copolymers.

11. A system for delivery of an active substance for release in the intestinal tract according to claim 10 wherein the active substance is a β-lactam antibiotic.

12. A system for delivery of an active substance for release in the intestinal tract according to claims 1 through 4 wherein the active substance is selected from the group consisting of analgesics, antibiotics, antidepressants, antivirals, antibodies, immuno-modulators, oncolytics, immunogens, hormones, vaccines, enzymes, nutrients and dietary fiber.

13. A system for delivery of an active substance for release in the intestinal tract comprising a particle having a core containing an active substance, said core being encapsulated by a first layer of a coating material consisting essentially of an enteric compound in an amount of about 10% to 70% of the total weight of the core and at least one material selected from the group consisting of plasticizers and anti-tackiness agents, such that said first coating layer is generally resistant to disintegration in human gastric juices but will disintegrate in human intestinal fluids, and said first coating layer being encapsulated by an exterior layer of a coating material consisting essentially zein in the amount of about 20% to 100% by weight of the sum of the weights of the core and the first coating layer and at least one material selected from the group consisting of plasticizers and hydrophobic substances.

14. A system for delivery of an active substance for release in the intestinal tract according to claim 13 wherein the enteric compound comprises at least one material selected from the group consisting of acids and esters of methacrylic copolymers.

15. A system for delivery of an active substance for release in the intestinal tract according to claim 14 wherein the zein has an ash content of not greater than about 2% by weight.

16. A system for delivery of an active substance for release in the intestinal tract according to any one of claims 13 through 15 wherein the active substance is selected from the group consisting of analgesics, antibiotics, antidepressants, antivirals, antibodies, immuno-modulators, oncolytics, immunogens, hormones, vaccines, enzymes, nutrients and dietary fiber.

17. A system for delivery of an active substance for release in the intestinal tract according to any one of claims 13 through 15 wherein the active substance is a β-lactam antibiotic.

18. A system for delivery of an active substance for release in the intestinal tract comprising a particle having a core containing an active substance, said core being encapsulated by a first layer of a coating material consisting essentially of zein in the amount of about 10% to 70% of the total weight of the core and at least one material selected from the group consisting of plasticizers and hydrophobic substances, and said first coating layer being encapsulated by a second coating layer consisting essentially of an enteric compound in an amount of about 10% to 70% of the sum of the weights of the core and the first coating layer and at least one material selected from the group consisting of plasticizers and anti-tackiness agents, such that said second coating layer is generally resistant to disintegration in human gastric juices but will disintegrate in human intestinal fluids.

19. A system for delivery of an active substance for release in the intestinal tract according to claim 18 wherein the particle is in the form of a tablet.

20. A system for delivery of an active substance for release in the intestinal tract according to either of claims 18 or 19 wherein the active substance is selected from the group consisting of analgesics, antibiotics, antidepressants, antivirals, antibodies, immuno-modulators, oncolytics, immunogens, hormones, vaccines, enzymes, nutrients and dietary fiber.

21. A system for delivery of an active substance for release in the intestinal tract according to either of claims 18 or 19 wherein the active substance is a β-lactam antibiotic.

22. A system for delivery of an active substance for release in the intestinal tract comprising a particle having a core containing an active substance, said core being encapsulated by a first layer of a coating material consisting essentially of zein in an amount of about 10% to 70% of the total weight of the core and at least one material selected from the group consisting of plasticizers and hydrophobic substances, said first coating layer being encapsulated by a second coating layer consisting essentially of an enteric compound in the amount of about 5% to 70% of the sum of the weights of the core and first coating layer and at least one material selected from the group consisting of plasticizers and anti-tackiness agents, such that said layer is generally resistant to disintegration in human gastric juices but will disintegrate in human intestinal fluids, and said second coating layer being encapsulated by an exterior coating layer of a coating material consisting essentially of zein in an amount of about 20% to 70% of the sum of the weights of the core and the first two coating layers and at least one material selected from the group consisting of plasticizers and hydrophobic substances.

23. A system for delivery of an active substance for release in the intestinal tract according to claim 22 wherein the zein has an ash content of not greater than about 2% by weight.

24. A system for delivery of an active substance for release in the intestinal tract according to claim 22 wherein the enteric compound comprises at least one material selected from the group consisting of acids and esters of methacrylic copolymers.

25. A system for delivery of an active substance for release in the intestinal tract according to claim 23 wherein the enteric compound comprises at least one material selected from the group consisting of acids and esters of methacrylic copolymers.

26. A system for delivery of an active substance for release in the intestinal tract according to any one of claims 22 through 25 wherein the active substance is selected from the group consisting of analgesics, antibiotics, antidepressants, antivirals, antibodies, immunomodulators, oncolytics, immunogens, hormones, vaccines, enzymes, nutrients and dietary fiber.

27. A system for delivery of an active substance for release in the intestinal tract according to any one of claims 22 through 25 wherein the active substance is a β-lactam antibiotic.

28. A system for delivery of an active substance for release in the intestinal tract comprising a liquid medium having a plurality of particles disposed therein, said particles comprising a core containing an active substance, said core being encapsulated by at least two layers of coating materials, one of said layers comprising a coating material, consisting essentially of zein and least one material selected from the group consisting of plasticizers and hydrophobic substances and the other layer comprising a coating material consisting essentially of an enteric compound and at least one material selected from the group consisting of plasticizers and anti-tackiness agents, such that said other layer is generally resistant to disintegration in human gastric juices but will disintegrate in human intestinal fluids, said particles having sizes of not greater than about 700 microns.

29. A system for delivery of an active substance for release in the intestinal tract according to claim 28 wherein said particles have a structure such that the core is encapsulated by a first layer comprising a coating material, consisting essentially of zein and at least one material selected from the group consisting of plasticizers and hydrophobic substances and said first layer is encapsulated by an exterior layer comprising a coating material consisting essentially of an enteric compound and at least one material selected from the group consisting of plasticizers and anti-tackiness agents, such that said second layer is generally resistant to disintegration in human gastric juices but will disintegrate in human intestinal fluids.

30. A system for delivery of an active substance for release in the intestinal tract according to claim 28 wherein said particles have a structure such that the core is encapsulated by a first layer comprising a coating material, consisting essentially of an enteric compound and at least one material selected from the group consisting of plasticizers and anti-tackiness agents, such that said first layer is generally resistant to disintegration in human gastric juices but will disintegrate in human intestinal fluids, and said first layer is encapsulated by an exterior layer comprising a coating material consisting essentially of zein and at least one material selected from the group consisting of plasticizers and hydrophobic substances.

31. A system for delivery of an active substance for release in the intestinal tract according to claim 28 wherein said particles have a structure such that the core is encapsulated by a first layer comprising a coating material, consisting essentially of zein and at least one material selected from the group consisting of plasticizers and hydrophobic substances and said first layer is encapsulated by a second layer comprising a coating material, consisting essentially of an enteric compound and at least one material selected from the group consisting of plasticizers and anti-tackiness agents, such that said second layer is generally resistant to disintegration in human gastric juices but will disintegrate in human intestinal fluids, and said second layer is encapsulated by an exterior layer comprising a coating material consisting essentially of zein and at least one material selected from the group consisting of plasticizers and hydrophobic substances.

32. A system for delivery of an active substance for release in the intestinal tract according to claim 28 wherein the zein has an ash content of not greater than about 2% by weight, and the enteric compound comprises at least one material selected from the group consisting of acids and esters of methacrylic copolymers.

33. A system for delivery of an active substance for release in the intestinal tract according to claim 29 wherein the zein has an ash content of not greater than about 2% by weight, and the enteric compound comprises at least one material selected from the group consisting of acids and esters of methacrylic copolymers.

34. A system for delivery of an active substance for release in the intestinal tract according to claim 30 wherein the zein has an ash content of not greater than about 2% by weight and the enteric compound comprises at least one material selected from the group consisting of acids and esters of methacrylic copolymers.

35. A system for delivery of an active substance for release in the intestinal tract according to claim 31 wherein the zein has an ash content of not greater than about 2% by weight, and the enteric compound comprises at least one material selected from the group consisting of acids and esters of methacrylic copolymers.

36. A system for delivery of an active substance for release in the intestinal tract according to any one of claims 28 through 35 wherein the liquid medium is an aqueous medium.

37. A system for delivery of an active substance for release in the intestinal tract according to any one of claims 28 through 35 wherein the active substance is selected from the group consisting of analgesics, antibiotics, antidepressants, antivirals, antibodies, immunomodulators, oncolytics, immunogens, hormones, vaccines, enzymes, nutrients and dietary fiber.

38. A system for delivery of an active substance for release in the intestinal tract according to either of claims 28 or 35 wherein the active substance is a β-lactam antibiotic.

39. A system for delivery of an active substance for release in the intestinal tract according to claim 36 wherein the active substance is an antibiotic.

40. A system for delivery of an active substance for release in the intestinal tract according to claim 36 wherein the active substance is a β-lactam antibiotic.

* * * * *

UNITED STATES PATENT AND TRADEMARK OFFICE
CERTIFICATE OF CORRECTION

PATENT NO. : 5,160,742

DATED : November 3, 1992

INVENTOR(S) : T. Mazer, G. Meyer, S. Hwang, E. Candler, L. Drayer and A. Daab-Krzykowski It is certified that error appears in the above-identified patent and that said Letters Patent is hereby corrected as shown below:

Column 3, Line 27, "table" should be --tablet--
Column 3, Line 64, "no" should be --not--
Column 9, Line 68, "C6-C~" should be --C6-C18--
Column 12, Line 19, should have the word --and-- inserted between "1.2" and "simulated"
Column 13, Line 25, "closing" should be --dosing--
Column 17, Line 20, "APP≜" should be --APP 24--
Column 25, Line 6, "62-Lactam" should be --β-Lactam--
Column 27, Line 66, "a6" should be --a 6--
Column 29, Line 51, "52.)" should be --52.0--
Column 30, Line 66, "the" should be --then--
Column 35, Line 37, "structure" should be --structures--
Column 36, Line 2, "AMCX" should be --AMX--
Column 36, Line 51, "as as" should be --as--
Column 27, Line 66, delete "a" (first occurrence).

Signed and Sealed this

Thirtieth Day of November, 1993

Attest:

BRUCE LEHMAN

Attesting Officer

Commissioner of Patents and Trademarks